(12) United States Patent  (10) Patent No.: US 7,771,984 B2
Dzekunov et al.  (45) Date of Patent: Aug. 10, 2010

(54) METHODS AND DEVICES RELATED TO A REGULATED FLOW ELECTROPORATION CHAMBER

(75) Inventors: Sergey Dzekunov, Germantown, MD (US); Nicholas Chopas, Germantown, MD (US); Linhong Li, North Potomac, MD (US)

(73) Assignee: Maxcyte, Inc., Gaithersburg, MD (US)

( * ) Notice: Subject to any disclaimer, the term of this patent is extended or adjusted under 35 U.S.C. 154(b) by 287 days.

(21) Appl. No.: 11/127,557

(22) Filed: May 12, 2005

(65) Prior Publication Data

US 2005/0282200 A1   Dec. 22, 2005

Related U.S. Application Data

(60) Provisional application No. 60/570,317, filed on May 12, 2004.

(51) Int. Cl.
 *C12M 1/42* (2006.01)
 *C12N 13/00* (2006.01)

(52) U.S. Cl. .................. 435/285.2; 435/173.6; 204/643

(58) Field of Classification Search .............. 435/173.6, 435/285.2
 See application file for complete search history.

(56) References Cited

U.S. PATENT DOCUMENTS

| | | | |
|---|---|---|---|
| 2,955,076 A | 10/1960 | Gossling | 435/446 |
| 3,676,325 A | 7/1972 | Smith et al. | 204/288 |
| 3,841,331 A * | 10/1974 | Wilder et al. | 604/152 |
| 4,075,076 A | 2/1978 | Xylander | 204/206 |
| 4,081,340 A | 3/1978 | Zimmermann et al. | 435/173.5 |
| 4,192,869 A | 3/1980 | Nicolau et al. | 514/76 |
| 4,252,628 A | 2/1981 | Boulton et al. | 204/257 |
| 4,321,259 A | 3/1982 | Nicolau et al. | 424/93.73 |
| 4,370,983 A | 2/1983 | Lichtenstein | 600/301 |
| 4,440,386 A | 4/1984 | Achelpohl | 271/70 |
| 4,473,563 A | 9/1984 | Nicolau et al. | 514/78 |
| 4,476,004 A | 10/1984 | Pohl | 435/285.2 |
| 4,478,824 A | 10/1984 | Franco et al. | 424/533 |
| 4,622,302 A | 11/1986 | Sowers | 435/450 |
| 4,652,449 A | 3/1987 | Ropars et al. | 424/533 |
| 4,663,292 A | 5/1987 | Wong et al. | 435/285.2 |
| 4,695,547 A | 9/1987 | Hilliard et al. | 435/285.2 |
| 4,699,881 A | 10/1987 | Matschke | 435/285.2 |

(Continued)

FOREIGN PATENT DOCUMENTS

AU   680890   10/1994

(Continued)

OTHER PUBLICATIONS

European Supplemental Search Report, issued in European Application No. 05748359.6-1521, mail date Oct. 21, 2009.

(Continued)

*Primary Examiner*—William H Beisner
(74) *Attorney, Agent, or Firm*—Fulbright & Jaworski L.L.P.

(57) ABSTRACT

The electroporation chamber and its related devices combine the features of an electroporation chamber that acts as a manifold for regulation of sample flow with those of a flow electroporation device to form a regulated flow electroporation device. The invention further comprises a novel regulated flow electroporation chamber that enables conditions in which a sample is uniformly processed in individual fractions or volumes in a fully closed (sterile) system.

14 Claims, 15 Drawing Sheets

U.S. PATENT DOCUMENTS

| | | | |
|---|---|---|---|
| 4,752,586 A | 6/1988 | Ropars et al. | |
| 4,764,473 A | 8/1988 | Matschke et al. | 435/285.2 |
| 4,784,737 A | 11/1988 | Ray et al. | 435/455 |
| 4,800,163 A * | 1/1989 | Hibi et al. | 435/285.2 |
| 4,804,450 A | 2/1989 | Mochizuki et al. | 435/285.2 |
| 4,822,470 A | 4/1989 | Chang | 435/450 |
| 4,840,714 A | 6/1989 | Littlehales | 204/464 |
| 4,849,089 A | 7/1989 | Marshall, III | 204/547 |
| 4,849,355 A | 7/1989 | Wong | 435/461 |
| 4,874,690 A | 10/1989 | Goodrich, Jr. et al. | 435/2 |
| 4,882,281 A | 11/1989 | Hilliard et al. | 435/285.2 |
| 4,906,576 A | 3/1990 | Marshall, III | 435/285.2 |
| 4,910,140 A | 3/1990 | Dower | 435/488 |
| 4,923,814 A | 5/1990 | Marshall, III | 435/173.6 |
| 4,931,276 A | 6/1990 | Franco et al. | 424/533 |
| 4,945,050 A | 7/1990 | Sanford et al. | 435/459 |
| 4,946,793 A | 8/1990 | Marshall, III | 435/285.2 |
| 4,956,288 A | 9/1990 | Barsoum | 435/6 |
| 4,970,154 A | 11/1990 | Chang | 424/93.21 |
| 4,995,268 A | 2/1991 | Ash et al. | 73/861.05 |
| 4,995,957 A | 2/1991 | Ziegler et al. | 204/458 |
| 5,007,995 A | 4/1991 | Takahashi et al. | 435/285.2 |
| 5,036,006 A | 7/1991 | Sanford et al. | 435/459 |
| 5,043,261 A | 8/1991 | Goodrich et al. | 435/2 |
| 5,098,843 A | 3/1992 | Calvin | 435/285.2 |
| 5,100,627 A | 3/1992 | Buican et al. | 422/108 |
| 5,100,792 A | 3/1992 | Sanford et al. | 435/459 |
| 5,114,681 A | 5/1992 | Bertoncini et al. | 422/111 |
| 5,124,259 A | 6/1992 | Tada | 435/470 |
| 5,128,257 A | 7/1992 | Baer | 435/173.6 |
| 5,134,070 A | 7/1992 | Casnig | 435/173.6 |
| 5,135,667 A | 8/1992 | Schoendorfer | 210/782 |
| 5,137,817 A | 8/1992 | Busta et al. | 435/207 |
| 5,139,684 A | 8/1992 | Kaali et al. | 205/701 |
| 5,232,856 A | 8/1993 | Firth | 435/285.2 |
| 5,422,272 A | 6/1995 | Papp et al. | 435/285.2 |
| 5,424,209 A | 6/1995 | Kearney | 435/286.5 |
| 5,501,662 A | 3/1996 | Hofmann | 604/20 |
| 5,505,685 A * | 4/1996 | Antwiler | 494/37 |
| 5,545,130 A | 8/1996 | Hofmann et al. | 604/6.11 |
| 5,612,207 A | 3/1997 | Nicolau et al. | |
| 5,676,646 A | 10/1997 | Hofmann et al. | 604/6.11 |
| 5,720,921 A | 2/1998 | Meserol | 422/44 |
| 5,728,281 A | 3/1998 | Holmstrom et al. | 600/347 |
| 6,074,605 A | 6/2000 | Meserol et al. | |
| 6,090,617 A | 7/2000 | Meserol | |
| 6,485,961 B1 | 11/2002 | Meserol | 435/285.2 |
| 6,773,669 B1 | 8/2004 | Holaday et al. | 422/44 |
| 2001/0001064 A1 | 5/2001 | Holaday | |
| 2003/0059945 A1 | 3/2003 | Dzekunov et al. | |
| 2003/0073238 A1 | 4/2003 | Dzekunov et al. | |
| 2004/0029240 A1 | 2/2004 | Acker | |
| 2005/0019311 A1 | 1/2005 | Holaday et al. | 424/93.7 |

FOREIGN PATENT DOCUMENTS

| | | |
|---|---|---|
| CA | 2214800 | 2/2002 |
| CN | 1195997 | 10/1998 |
| DE | 2405119 | 9/1975 |
| DE | 3603029 | 8/1987 |
| DE | 4440386 | 5/1996 |
| EP | 0137504 | 4/1985 |
| EP | 0343783 | 11/1989 |
| EP | 0362758 | 4/1990 |
| EP | 0472772 | 3/1992 |
| EP | 0798309 | 10/1997 |
| JP | 62151174 | 7/1987 |
| JP | 62171687 | 7/1987 |
| JP | 62228277 | 10/1987 |
| JP | 62265975 | 11/1987 |
| JP | 63141587 | 6/1988 |
| JP | 1141582 | 6/1989 |
| JP | 2131584 | 5/1990 |
| JP | 2131585 | 5/1990 |
| JP | 2186993 | 7/1990 |
| JP | 3195485 | 8/1991 |
| JP | 4027393 | 1/1992 |
| JP | 63049068 | 12/1994 |
| JP | 7180029 | 7/1995 |
| JP | 7320720 | 12/1995 |
| WO | WO 88/04322 | 6/1988 |
| WO | WO 89/02464 | 3/1989 |
| WO | WO 89/03426 | 4/1989 |
| WO | WO 91/18103 | 11/1991 |
| WO | WO 94/21117 | 9/1994 |
| WO | WO 96/28199 | 9/1996 |
| WO | WO 98/24490 | 6/1998 |
| WO | WO 99/62592 | 12/1999 |
| WO | WO 01/24830 | 4/2001 |

OTHER PUBLICATIONS

U.S. Appl. No. 09/397,303, filed Sep. 15, 1999, Holaday et al.

"Advanced Coatings for the Medical Industry," Multi-Arc Scientific Coatings, Copyright © Andal Corp.

"Biological Buffers," In: *The Biological Engineering Handbook*, Bronzino (ed.), CRC Press, pp. 1650, c1995.

"Final Office Action," issued is U.S. Appl. No. 09/707,928, dated Sep. 25, 2003.

"Ion Bond® 16 Zirconium Nitride Coating," Multi-Arc, Inc., 1996.

"Ion Bond® 17 Titanium Aluminum Nitride Coating," Multi-Arc, Inc., 1995.

"Ion Bond® 19 Chromium Nitride Coating," Multi-Arc, Inc., 1995.

"Ion Bond® Coatings for Instruments, Design Considerations," Multi-Arc, Inc., 1995.

"Ion Bond® Coatings for Instruments, Most Commonly Asked Questions," Multi-Arc, Inc., 1995.

"Non-final Office Action," issued in U.S. Appl. No. 09/707,928, dated Aug. 15, 2002.

"Non-final Office Action," issued in U.S. Appl. No. 09/397,303, dated May 23, 2000.

"Non-final Office Action," issued in U.S. Appl. No. 10/846,729, dated Jul. 31, 2006.

"Non-final Office Action," issued in U.S. Appl. No. 10/846,729, dated Jan. 24, 2007.

"Notice of Allowance and Fee(s) Due," issued in U.S. Appl. No. 09/707,928, dated Jan. 5, 2004.

"Preparation of certain reagents, anticoagulants and preservative solutions," In: *Practical Haematology*, 5th Edition, Dacie and Lewis (eds.), Appendicies, pp. 598, 1975.

"The Ion Bond Network," Multi-Arc, Inc., 1995.

Abatti et al., "Development of a new geometrical form of micropipette: electrical characteristics and an application as a potassium ion selective electrode," *IEEE Trans. Biomed. Eng.*, 39:43-48, 1992.

Asakami et al., "Materials for electrode of alkali metal thermoelectric converter (AMTEC) (II)," *J. Mater. Sci. Lett.*, 9(8):892-894, 1990.

Behrndt and Lunk, "Biocompatibility of TiN preclinical and clinical investigations," *Materials Sciences & Engineering*, A139:58-60, 1991.

Capizzi et al., "Amifostine mediated protection of normal bone marrow from cytotoxic chemotherapy," *Cancer*, 72:3495-3501, 1993.

Chassy et al., "Transformation of bacteria by electroporation," *Trends in Biotechnology*, 6(12):303-309, 1988.

Coll et al., "Metallurgical and Tribological modification of titanium and titanium alloys by plasma assisted techniques," *Workshop H Society for Biomaterials Implat Retrieval Symposium*, Sep. 17, 1992.

Dunican and Shivnan, "High frequency tranformation of whole cells of amino acid producing coryneform bacteria using high voltage electroporation," *Bio/Technology*, 7:1067-1070, 1998.

Egorov and Noikova, "Effect of phase composition of TiN-Ni sintered electrode materials of characteristics of the ESA process," *Sov. Powder Metall Met. Ceram.*, 29(9):705-710, 1991.

Einck and Holaday, "Enhancement of tissue oxygenation by intracellular introduction of inositol hexaphosphate by flow electroporation of red blood cells," In: *Tissue Oxygenation in Acute Medicine*(*Update in Intensive Care and Emergency Medicine*, 33), Sibbald et al., (eds.), pp. 357-374, c1998.

Gersonde and Nicolau, "Enhancement of the $O_2$ release capacity and of the Bohr-effect of human red blood cells after incorporation of inositol hexaphosphate by fusion with effector-containing lipid vesicles," In: *Origins of Cooperative Binding by Hemoglobin*, 277-282, 1982.

Gersonde and Nicolau, "Improvement of the red blood cell $O_2$ release capacity by lipid vesicle-mediated incorporation of inositol hexaphosphate," *Blut*, 39:1-7, 1979.

Gersonde and Nicolau, "Modification of the oxygen affinity of intracellular haemoglobin by incorporation of polyphosphates into intact red blood cells and enhanced $O_2$ release in the capillary system," *Biblthca Haemat.*, 46:81-92, 1980.

Gersonde and Weiner, "The influence of infusion rate on the acute intravenous toxicity of phytic acid, a calcium-binding agent," *Toxicology*, 22:279-286, 1982.

Hirai et al., "A new antitumor antibiotic, FR-900482" *J. of Antibiotics*, 40/5:607-611, 1987.

Hofmann and Evans, "Eletronic genetic—physical and biological aspects of cellular electromanipulation," *IEEE Engineering in Medicine and Biology Magazine*, 6-11, 19-22, 1986.

Kinosita and Tsong, "Voltage-induced conductance in human erythrocyte membranes," *Biochimica et Biophysica Acta*, 554:479-497, 1979.

Kobayashi et al., "Fabrication of zirconim nitride sintered bodies and the application for electrode materials," *J. Ceram. Soc. Jpn.*, 97(10):1189-1194, (with English summary), 1989.

Kullmann et al., "In vitro effects of pentoxifylline on smooth muscle cell migration and blood monocyte production of chemotactic activity for smooth muscle cells: potential therapeutic benefit in the adult respiratory distress syndrome," *Am J. Respir. Cell*, 8:83-88, 1993.

Kurtz and Gordon, "Transparent conducting electrodes on silicon," *Sol. Energy Mater.*, 15(4):229-236, 1987.

Lehninger (ed.), In: *Principles of Biochemistry*, Chapter 8: 181-194, 1982.

Maurer et al., "Reduction of fretting corrosion of Ti-6Al-4V by various surface treatments," *J. Orthop. Res.*, 11:865-873, 1993.

Merz et al., "Determination of HIV infection in human bone," *Unfallchirurg*, 941:47-49, (with English summary), 1991.

Mouneimne et al., "Stable rightward shifts of the oxyhemoglobin dissocation curve induced by encapsulation of inositol hexaphosphate in red blood cells using electroporation," *FEBS Letters*, 275:117-120, 1990.

Narayan et al., "Diamond, diamond-like and titanium nitride biocompatible coatings for human body parts," *Materials Sciences & Engineering*, B25:5-10, 1994.

Nicolau et al., "Incorporation of allosteric effectors of hemoglobin in red blood cells. Physiological effects," *Biblthca haemat.*, 51:92-107, 1985.

Nicolau et al., "Short- and long-term physiological effects of improved oxygen transport by red blood cells containing inositol hexaphosphate," In: *Phytic Acid: Chemistry and Applications*, Graf (ed.), Chapter 16:265-290, 1986.

Pietra et al., "Titanium nitride as a coating for surgical instruments used to collect human tissue for trace metal analysis," *Analyst*, 115:1025-1028, 1990.

Ropars et al., "Improved oxygen delivery to tissues and iron chelator transport through the use of lysed and resealed red blood cells: a new perspective on cooley's anemia therapy," *Annals New York Academy of Sciences*, 445:304-315, 1985.

Satomi et al., "Tissue response to implanted ceramic-coated titanium alloys in rats," *J. Oral Rehab.*, 15:339-345, 1988.

Schaldach et al., "Pacemaker electrodes made of titanium nitride," *Biomed Technik.*, 34:185-190, 1989, with English abstract.

Shoji et al., "New fabrication process for Josephson tunnel junctions with (niobium nitride niobium) double-layered electrodes," *Appl. Phys. Lett.*, 41(11):1097-1099, 1982.

Susuki, "Biomedical electrode with silicon nitride film," *Jpn. J. Med. Electron. Biol.*, 19(2):114-119, (with English summary), 1981.

Taheri et al., "A dry electrode for EEG recording," *Electroencephalography and Clinical Neurophysiology*, 90(5):376-383, 1994.

Tait and Aita, "Aluminum nitride as a corrosion protection coating for steel: self-sealing porous electrode model," *Surf. Eng.*, 7(4):327-330, 1991.

Teisseire et al., "Physiological effects of high-$P_{50}$ erythrocyte transfusion on piglets," *J. Appl. Phys.*, 58:1810-1817, 1985.

Teisseire et al., "Significance of low hemoglobin oxygen affinity," 153-159.

Teissere et al., "Long-term physiological effects of enhanced $O_2$ release by inositol hexaphosphate-loaded erythrocytes," *Proc. Natl. Acad. Sci., USA*, 84:6894-6898, 1987.

Therin et al., "A histomorphometric comparison of the muscular tissue reaction to stainless steel, pure titanium and titanium alloy implant materials," *J. Materials Science: Materials in Medicine*, 2:1-8, 1991.

Vasilenko et al., "Preparation of porous electrodes from titanium nitrides," *Poroshkovaia Metallurgiia*, 13:39-42, 1973, article in Russian, (with English summary).

Weiner, "Right shifting of Hb-$O_2$ dissociation in viable red cells by liposomal technique," *Biol. of the Cell*, 47:65-70, 1983.

Weisel et al., "Adverse effects of transfusion therapy during abdominal aortic aneurysectomy," *Surgery*, 83:682-690, 1978.

Wisbey et al., "Application of PVD TiN coating to Co-Cr-Mo based surgical implants," *Biomaterials*, 8:477-480, 1987.

Wisbey et al., "Titanium release from TiN coated implant materials," *ImechE*, C384/042:9-14, 1989.

Zhao et al., "Direct current (dc)-plasma CVD equipment with auxiliary heating electrodes," *Vacuum*, 42(17):1109-1111, 1991.

Zhu et al., "Fabrication and characterization of glucose sensors based on a microarray hydrogen peroxide electrode," *Biosensors and Bioelectronics*, 9(4-5):295-300, 1994.

Chinese Office Action, issued in Chinese Application No. 200580015262.4, mailed Apr. 13, 2010 (English translation included).

* cited by examiner

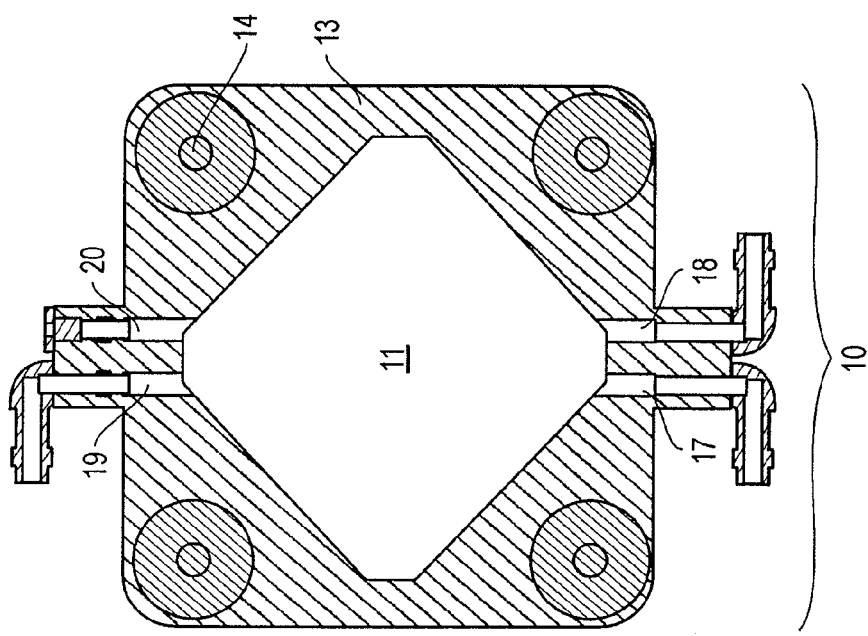
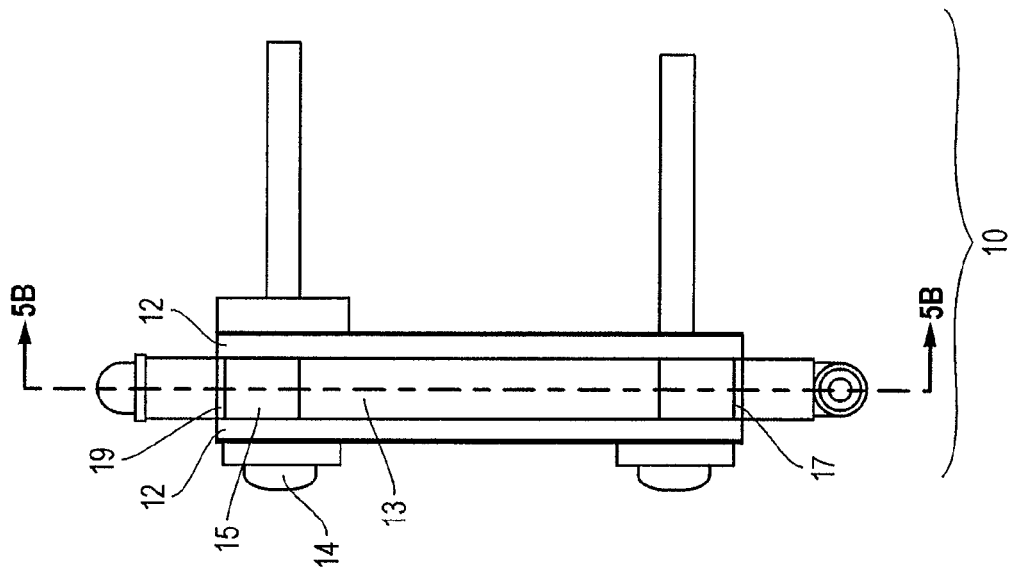

METHODS AND DEVICES RELATED TO A REGULATED FLOW ELECTROPORATION CHAMBER

This application claims priority to U.S. Provisional Patent application Ser. No. 60/570,317, filed on May 12, 2004, which is incorporated herein by reference in its entirety.

BACKGROUND OF THE INVENTION

I. Field of the Invention

The present invention relates generally to the field of treating cells with transient electric fields and more particularly to electroporation of cells. More particularly, it concerns methods for regulated flow electroporation, an electroporation chamber and related devices.

II. Description of Related Art

Electroporation has been used for the insertion of molecules into animal or plant cells since the early 1970's. Researchers have demonstrated that exposure of cells to a short duration, high voltage electrical field causes openings to form in the cell membrane through which molecules, including macromolecules such as proteins and DNA, can enter the cell. These openings, referred to as electropores, are regions of increased permeability initiated by local breakdown in the cell membrane caused by high voltage electric fields. These pores exist transiently but long enough for macromolecules such as plasmid DNA molecules to enter the cells. While cells can tolerate the creation of these pores, the process of creating them and introducing molecules can, if carried out to excess, kill the cells. Since this electroporation involves passing a current (albeit briefly) through the conductive cell suspension the electrodes generate heat in accordance with Joule's Law. This heat can increase the temperature of the cell suspension and, if excessive, raise the temperature of the cells to a point where the cells die.

Most early applications of electroporation were carried out using specialized cuvettes containing electrodes positioned relative to one another so that a substantially uniform electric field can be generated between them. Most conveniently, this is provided by two flat plate electrodes attached to opposite walls of a rectangular cuvette or chamber. A suspension of cells to be electroporated combined with a molecule or molecules that the operator desired to introduce into the cells is placed in the cuvette or chamber, which is then placed between the electrodes such that the cell suspension comes into in fluid contact with the electrodes. To effect electroporectic introduction of the molecules into the cells, an electric field pulse of high voltage and short duration was applied one or more times to the electrodes and thereby to the cell suspension between the electrodes. Most commercially available electroporation cuvettes are limited in capacity and can only process small amounts of cell suspension at a time (usually less than one ml). Given the small volumes of cells that could be electroporated per loading of a cuvette, electroporation of large volumes of cell suspension was impractical.

Typically, maintenance of sterility is essential for nearly all applications of electroporation of large volumes of cells. Relative to the maintenance of sterility, repeated loading of a cuvette and pooling of the electroporated cells is especially impractical. While this method of electroporation is convenient and simple and met the needs of many researchers carrying out small scale electroporation of cells additional methods were needed, especially methods that could conveniently facilitate the electroporation of large volumes of cells while maintaining a sterile environment. Electroporation of large volumes of cells in a closed sterile system would enable the use of electroporation for cell based therapy of humans. A method and apparatus that creates and maintains a closed sterile fluid path throughout the operation is therefore most desired.

In the 1980's, work was initiated by several researchers on flow electroporation for processing large volumes of cells (U.S. Pat. Nos. 4,752,586, 5,612,207, 6,074,605, 6,090,617, each of which is incorporated herein in its entirety by reference). Flow devices for electroporation generally consisted of parallel electrodes between which the cell suspension to be electroporated continuously and steadily flowed until the entire volume of cells had been electroporated. As the cell suspension steadily flowed between the electrodes, a high voltage pulse was applied to the cells. Repeated application of high voltage pulses to the electrodes resulted in the generation of heat and it was found to be necessary to remove this heat by a cooling means to prevent the electrodes and the cell suspension from reaching too high a temperature. The apparatus for flow electroporation contain an electroporation chamber having the electrodes and the ports through which cell suspension can be pumped. The electrodes are connected electrically to electronic circuitry that is capable of providing high voltage pulses to the electrodes. The high voltage pulses can be controlled by a programmable computer. Flow electroporation systems have been developed that are capable of electroporating larger volumes of cells, enabling production of viable cells into which a desired molecule had been introduced.

The conditions for electroporation vary from cell type to cell type and can vary according to the type of molecule one desires to introduce into the cells. For any particular cell type an optimal process exists consisting of an optimal number pulses of optimal voltage and duration spaced at optimal intervals. In order to apply the optimal number of electrical pulses to the cells, when using a flow electroporation apparatus described in the art, the rate of flow of the cell suspension through the electroporation chamber and between the electrodes, as well as the rate of pulsing is chosen to provide the optimal number of pulses to a volume of cell suspension. For example, if the optimal number of pulses per cell is known to be two per unit time for a particular cell, and the volume through the electroporation chamber is one milliliter, then the flow rate is set to one milliliter per unit time and the two pulses are applied per unit time. In this way on average, each cell will receive two pulses in this example. However, the hydrodynamic flow of the cell suspension through the electroporation chamber does not result in every cell traveling through the chamber and between the plates at the same rate. Since the rate of flow is higher away from the chamber walls than near the chamber walls a cell that flows between the electrodes toward the center of the fluid flow will pass between the electrodes in less than the unit time, and may receive fewer than two pulses, while a cell that flows near a wall may take longer than the unit time to pass between the electrodes and thereby receive more than two pulses. Since in this example two pulses are optimal for every cell, clearly not every cell receives the optimal number of pulses and the overall electroporation of the cell suspension is less than optimal.

As mentioned above, electroporation inherently results in the production of heat in the cell suspension, according to Joule's Law. Since in a flow electroporation method in which flow is steady and continuous, heating is substantially continuous the means to remove heat from the electroporation chamber must be capable of balancing the production of heat to avoid having the temperature of the chamber rise to an unacceptable temperature. The continuous nature of the process does not provide for periods during which cooling can be provided between periods of electroporation.

As discussed above the optimal conditions for electroporation are likely to vary according to the particular cell type being electroporated and the type of molecule one desires to introduce into the cell by electroporation. It is possible to experimentally address this question by systematically varying electroporation conditions using static cuvettes and then apply the optimal conditions determined from these experiments to a flow electroporation system. This approach suffers from two drawbacks. First, since static cuvette electroporation of a large number samples is time consuming the cells used for each static electroporation will vary through the experiment. Second, using this approach one assumes, but does not know, that the optimal conditions for static cuvette electroporation will be the same as flow electroporation. It would be desirable to be able to optimize electroporation conditions rapidly using a single sample of cells for all experimental electroporation conditions while also using the same apparatus that later would be used for large-scale electroporation of cells for therapeutic or other applications.

Certain molecules, most notably mRNA, may be unstable in the presence of cells into which one desires to introduce the molecule by electroporation. In the case of mRNA, this is likely to be the result of ribonucleases present in the cell culture media or on the surface of the cells. In such cases, it is desirable to minimize the time during which the molecule will be in this unstable condition prior to its introduction into the cell. With static cuvette based electroporation the molecule (e.g., mRNA) is mixed with the cells and then manually loaded into the cuvette, whereupon following installation in the electroporation apparatus electroporation is carried out. During the time required to carry out these manual steps some of the molecules added to the cells may be destroyed. A method whereby the molecules to be introduce can be automatically mixed with cells immediately prior to electroporation and in a closed sterile environment is desirable.

In a continuous flow system described in the art, apart from coordinating the application of pulses to the electrodes with the initiation of flow of cells between the electrodes there is no "during process" coordination between pulsing and flow of the cells.

A method and apparatus that combines the advantages of continuous flow electroporation, particularly the ability to electroporate large volumes of cells in a sterile closed system while assuring that every cell receives the optimal number of pulses, is desirable.

SUMMARY OF THE INVENTION

Embodiments of the invention include electroporation methods, as well as related electroporation devices and apparatus capable of large volume electroporation. In certain aspects, the invention is capable of balancing the production of heat to avoid having the temperature of the chamber rise to an unacceptable temperature. In addition, the electric pulses may be optimized for the processing of an individual unit volume and/or the processing of all or parts of a sample of interest. As used herein "unit volume" or "unit" is a volume of sample or fluid that fills or partially fills an electroporation chamber. A unit is typically that portion of sample that is exposed to a particular electric pulse or series of pulses. Each unit may be referred to as being a fraction or part of the sample. The unit may be determined by the operator and is regulated by the filling and emptying of the electroporation chamber or by variation in the rate of flow through chamber. Each unit may be a distinct individual fraction of the sample produced by the introduction of a non-sample gas or liquid between two or more units of sample. In various embodiments, processing of a sample is carried out in closed system, i.e., a system with limited exposure to the environment external to the interior of the device or apparatus containers, fluid paths, and chambers of an electroporation device. Such closed system may be used to maintain the sterility and integrity of a sample.

Embodiments of the invention include flow-electroporation processes comprising regulating sample flow through an electroporation chamber. Typically, the sample is processed in units that are produced by a repeated cyclic filling and emptying of the electroporation chamber. Each sample unit cycled through the electroporation chamber may be exposed to the same or different electric pulses or conditions. In certain aspects, the units of sample are produced by providing a boundary between unprocessed and processed volumes of the sample. The boundary may be provided by cycling a non-sample gas or fluid into the chamber between two or more units or fractions of the sample. A non-sample gas or liquid will typically be displaced from the chamber by a volume of unprocessed sample. The non-sample fluid or gas may flow into the chamber by evacuation of the processed sample from the electroporation chamber, active pumping of sample into the electroporation chamber, active pumping of the non-sample fluid or gas into the electroporation chamber, or various combinations thereof.

"Pumping" refers to providing a pressure gradient that imparts a motive force to a fluid or gas. Such a motive force, for example, may be provided by gravity or forces associated with the surface tension of the fluid being pumped. The means for imparting a motive force on a gas or liquid, in particular for moving a cell suspension, is referred to as a pumping means. Pumping means include a variety of mechanisms to cause pressure differentials in the system to regulate the flow of fluid or gas within the flow paths. A variety of pumping means are known, including, but not limited to rotary, reciprocating, centrifugal, airlift, or jet pumps. A pumping means may include piston, plunger, peristaltic, diaphragm, variable volume container, compressed gas, propellers, turbines, screw, or gear type mechanisms to produce a regulated flow of fluid or gas.

In particular aspects, the cycling is produced by alternating sample flow through 1, 2, 3, 4, or more ports in the electroporation chamber. A "port" refers to any opening through which fluid may flow into or out of the electroporation chamber. It is contemplated that the electroporation chamber may be used as a manifold for directing fluid flow, but other embodiments contemplated may or may not use a manifold that is not part of the electroporation chamber. Cycling of the sample and non-sample fluid or gas will typically be regulated by various combinations of 1, 2, 3, 4, 5, 6, or more pumping means, valves or other fluid regulating mechanisms. In one example, a boundary may be provided by dripping a sample through a chamber, wherein a drop of sample is exposed to one or more electric pulses as it transits between two electrodes.

Further embodiments of the invention include flow electroporation chambers comprising a chamber containing at least two electrodes; and at least three ports, wherein (i) a first port is for sample flow into a chamber; (ii) a second port is for processed sample flow out of the chamber; and (iii) a third port is for non-sample fluid or gas flow in or out of the chamber, wherein the non-sample fluid or gas flows out of the chamber when a sample flows into the chamber and the non-sample fluid or gas flows into the chamber when processed sample flows out of the chamber. The first port may be in fluid communication with one or more sample containers. The second port may be in fluid communication with one or more processed sample containers. The third port may be in fluid communication with a reservoir container, wherein the reservoir container contains all or part of the non-sample fluid or gas volume when the chamber is filled or partially filled with a sample volume. In certain embodiments, the chamber may have at least four ports. The fourth port may be in fluid communication with the sample container, the processed sample container, the non-sample gas or fluid reservoir, a reagent container (e.g., wash buffer, cleaning solution, cooling solution, etc.) or various combinations thereof.

In further embodiments, flow electroporation devices may comprise at least 1, 2, 3, 4 or more sample containers in fluid communication with an electroporation chamber through a first chamber port, forming a first fluid path; at least 1, 2, 3, 4, or more processed sample containers in fluid communication with the electroporation chamber through a second chamber port, forming a second fluid path; and at least one non-sample fluid or gas reservoir in fluid communication with the electroporation chamber through a third chamber port, forming a third fluid path. The non-sample gas or fluid reservoir may be a non-sample gas or fluid container, part of the sample container, part of the processed sample container, part of the electroporation chamber, or various combinations thereof. The second fluid path may be in fluid communication with one or more sample container of the first fluid path and the non-sample reservoir of the third fluid path distal to the position of the electroporation chamber in relation to the processed sample container in the second fluid path. In certain aspects the device may further comprise at least 1, 2, 3, 4 or more pumps operatively coupled to at least 1, 2, 3, 4, or more fluid paths. The sample container, processed sample container, non-sample fluid or gas reservoir, or various combinations thereof may be a collapsible, expandable, or fixed volume containers. In further aspects of the invention, fluid flow in the device may be directed by the opening or closing of 1, 2, 3, 4, 5, 6, or more or more fluid paths of the device. Various fluid paths may be alternatively open and closed, preferably the flow path from the sample container to the electroporation chamber and the flow path from the electroporation chamber to the processed sample container are alternatively opened and closed, wherein neither is open at the same time during electroporation cycling. The fluid flow may be modulated by 1, 2, 3, 4, 5, 6, or more valves, 1, 2, 3, 4, 5, 6, or more pumping means, or various combinations thereof. In a preferred embodiments a pump is a peristaltic pump, and more preferably, the peristaltic pump is a full compression peristaltic pump.

In still further embodiments, a flow electroporation device may comprise at least 1, 2, 3, 4 or more sample containers in fluid communication with an electroporation chamber through a first chamber port and the electroporation chamber is in fluid communication with the sample container through a second chamber port, forming a first fluid path; at least 1, 2, 3, 4, or more processed sample container is in fluid communication with the electroporation chamber through a third chamber port and the electroporation chamber is in fluid communication with the processed sample container through a fourth chamber port, forming a second fluid path. The 1, 2, 3, 4, or more processed sample container may also be used as a non-sample gas or fluid reservoir. In certain aspects, the non-sample gas or fluid reservoir is combined with the sample container, the processed sample container or both the sample container and the processed sample container. The device may also comprise at least 1, 2, 3, 4, or more pumping means operatively coupled to at least 1, 2, 3, 4, 5, 6 or more fluid paths. The sample container, processed sample container, or both containers may be a collapsible, expandable or fixed volume container. In various aspects, the fluid flow in the device is directed by the opening or closing of one or more fluid paths of the device. In certain embodiments, first and second fluid paths are alternatively open and closed. The fluid flow is typically modulated or regulated by one or more pumping means, preferably a pump, more preferably a peristaltic pump, and still more preferably a peristaltic pump that is a full compression peristaltic pump. Fluid flow may also be regulated or modulated by various combinations of valves, pumping means or combinations thereof.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternative are mutually exclusive, although the disclosure supports a definition that refers to only alternatives and "and/or."

Other objects, features, and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 5 is a diagram of one embodiment of an electroporation chamber.

FIG. 12A is control transfection. FIG. 12B is 400 μL static transfection. FIG. 12C is a 100 mL variable flow transfection.

DESCRIPTION OF ILLUSTRATIVE EMBODIMENTS

Figure 1:
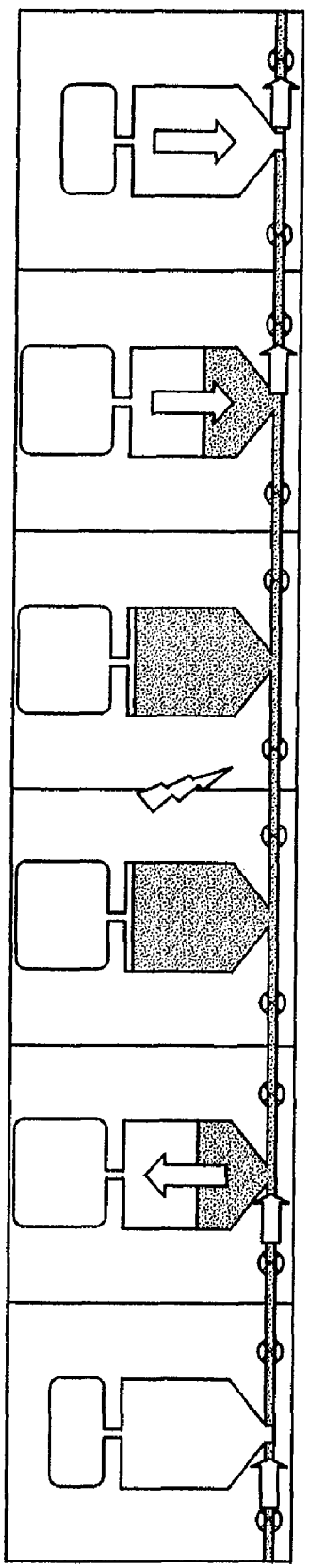
FIG. 1 is a schematic of an exemplary cycle of the electroporation process.

Embodiments of the invention include various new apparatus and methods for electroporation. In particular, certain embodiments provide for flow electroporation devices and methods for introducing molecules, compounds or compositions into cells or fragments of cells, including, but not limited to, bacteria, fungi, plant cells, animal cells, cultured cells, primary cells, red blood cells, white blood cells, platelets, stem cells, genetically engineered stem cells, or an expanded population of stem cells. In certain aspects, a transient high voltage electric fields can disturb the metabolism of cells and kill some cells if applied at too high a voltage or for too long a duration. Since different cell types can be differentially affected by transient electric fields treatment with transient electric fields, such as those used to load or introduce molecules into cells by electroporation different cells in a population of cells may be differentially killed and thereby purged from the population. In other aspects, a molecule need not be introduced, but the sample treated by exposure to an electric field. In still other embodiments, the object may not be the introduction of a foreign molecule into the cell, but rather modification of treated cells, i.e., cells exposed to some other pharmacologic agent or condition before, during or after exposure to an electric field—killing being an extreme case of modification. In one embodiment, a device of the invention combines an electroporation chamber within which cells are electroporated with a regulated or variable flow of cell suspension within the apparatus, which allows for the repeated filling and emptying of an electroporation chamber coordinated with electric pulsing. Preferably, the chamber and its related flow paths and containers can form a closed sterile environment. Other advantages conveyed by the present invention include the ability of the apparatus to provide a more uniform pulsing of the cells. The novel regulated flow electroporation chamber allows volumes of cell suspension to be electroporated in unit volumes. Individual fractions or unit volumes are defined volumes of sample flowing through the electroporation chamber that may be physically separated by a non-sample gas or fluid or may be separated from one another by other means such as the opening and closing of a valve. This separation between sample volumes facilitates the segregated collection of each separate volume in such cases in which successive volumes may not have experienced the same electroporation conditions or in which successive volumes may have comprised different combinations of cells and molecules for electroporetic loading. It is contemplated that the method and apparatus, including the electroporation chamber of the present invention, may be used to encapsulate a variety of substances in a variety of cell populations, as well exposing cells to an electric field that have been exposed, are being exposed or will be exposed to a pharmacologic agent or condition. The exposure to an electric field may in and of itself be a treatment of the cells.

Certain embodiments of the invention include processing methods where there is a regulated flow of fluids or gas through the chamber. Thus, this processing method may be referred to as continuous flow. However, in certain embodiments the flow of sample or processed sample may slow or stop intermittently during the process so that continuous is descriptive of the fluid or gas flow through the chamber as a whole and not necessarily any particular sample, fluid or gas. The electroporation process typically comprises flow of sample through a chamber wherein the sample is processed in defined individual fractions or unit volumes. Each individual fraction may be demarcated by a volume of non-sample fluid or gas flowing into the electroporation chamber between an electroporation of different portions of the cell suspension.

In some embodiments, a sample may be processed into multiple product fractions. Furthermore, each processed sample fraction may be sorted, collected, and/or stored individually or in specified groups. A product or processed sample fraction(s) may be a combination of several samples processed together or one at a time. There is nothing in the present invention that interferes with a user of this technology to partially fill the chamber with one sample, then add additional solution, carry out electroporation, and collect resulting product.

In certain aspects of the invention, individual sample fractions may be exposed to different pulses or reagents. For example, initially all or a portion of a sample, or a sample of similar composition, may be processed using a range of conditions to quickly optimize the electroporation conditions. Alternatively, the user may wish to produce a population of cells or individual fractions of cells that contain cells that have been exposed to various electroporation conditions.

In certain embodiments, "online mixing" of sample components is contemplated. For example, certain reagents may be either unstable or harmful to cells or other electroporation targets or reagents in an electroporation mixture. Thus, it is desirable to bring such components together just before an electric pulses is applied, i.e., no advance mixing or only a short period of time between mixing of one or more component of the electroporation sample prior to electroporation.

Further embodiments of the invention comprise a novel regulated flow electroporation chamber that allows for the regulated flow of cells into and out of the electroporation chamber such that flow into and out of the chamber is at a substantially lower rate when cells receive high voltage pulses than between pulses or a series of pulses. The flow of cells need not necessarily be reduced to zero to achieve the advantages of regulated flow but reduced flow during electroporation is desired. Embodiments of the invention further provide for temporal coordination between the electronic components providing high voltage pulses to the electrodes and means for flowing the cell suspension between the electrodes. The means for flowing (providing a motive force to a fluid or gas) the cell suspension is referred to as a pumping means. Pumping means include a variety of mechanisms to cause pressure differentials in the system to regulate the flow of fluid or gas within the flow paths. A variety of pumping means are known, including, but not limited to gravity, rotary, reciprocating, centrifugal, airlift, or jet pumps, which may also include piston, plunger, peristaltic, diaphragm, variable volume container, compressed gas, propellers, turbines, screw, or gear type mechanisms to produce a regulated flow of fluid or gas.

The present invention may further provide a convenient means to cool the electroporation chamber between electroporation of cell suspension volumes. The time between filling and emptying of the electroporation chamber with a cell suspension may be adjusted to assure that the temperature of the electroporation chamber is not above a certain temperature prior to introducing cell suspension for electroporation.

Additional modifications to the basic designs may also be included in accordance with the main principles described herein. In various embodiments, the sample and product lines or fluid paths meet only in the cavity of the chamber, i.e., the chamber acts as a manifold for sample flow, and the chamber can be completely or partially emptied before the new sample fraction arrives. "Fluid path," as used herein, refers to an assembly of components or portion thereof, that are in fluid communication by means of any channel, tube, pipe and/or pathway, through which a fluid, such as a liquid or a gas, may pass. As used herein, "fluid communication" refers to a functional connection, either direct or indirect, between two or more components of a fluid path that may allow fluids to pass between the components and within the fluid path. For example, a sample container is in "fluid communication" with a chamber if fluid may pass from the sample container to the chamber.

An example of a fluid path that can be in fluid communication is a path that includes a container and a chamber connected by a tubing with a device for regulating the flow of fluid or gas through the path, such a device may include a full compression peristaltic pump or a valve positioned between the container and the chamber. A regulating device may be operatively coupled at any position between the container and the chamber. The term "operatively coupled," as used in the context of a flow regulating device, refers to an indirect or direct communication between the regulating device and a fluid or gas such that the flow of the fluid or gas is regulated in some manner, e.g. allowing or inhibiting flow. The regulating device need not be in direct contact with the fluid or gas, e.g., a pinch valve on flexible tubing (see FIG. 15 for example).

In certain embodiments, one or more fluid paths of the device may be an aseptic path. That is, flow of sample from a sample source(s) and the flow of processed sample from the chamber to the processed sample container(s) may be a closed system. The closed system may be prepared under appropriate aseptic conditions so that during processing the sample remains aseptic. Furthermore, containers, tubes, electroporation chambers, and the like may be disposable. As used herein "disposable" refers to components that by virtue of their design and fabrication may be sufficiently inexpensive to make that many, if not most, users would find it economically efficient to not reuse the component and to dispose of the component following a single use.

Various other process components may be included in devices and methods of the invention. For example, a solution source, e.g., flush buffer source, may be added for flushing, cleaning, or cooling the chamber between cycles or after a certain number of cycles. A flushing buffer may also be used to cool the electrodes and the chamber at intervals.

I. Description of Flow Electroporation Methods

FIG. 1 is a schematic that represents an exemplary electroporation cycle of a method of regulated or intermittent flow electroporation described herein. Panel one illustrates the removal of a non-sample fluid or gas from the chamber, with panel two illustrating the concomitant filling of the chamber with a sample to be electroporated. Panels three and four illustrate the electroporation of the sample during transition from in-flow to out-flow of the sample. Panels five and six illustrate the concomitant in-flow of non-sample fluid or gas as the processed sample is removed from the chamber. Aspects of the invention include in-flow, out-flow or both in-flow and out-flow occurring through 1, 2, 3, 4, 5, 6 or more ports of the electroporation chamber. In-flow and out-flow may be through same or different ports. The chamber itself may be used as a manifold or a separate manifold may be positioned external to the chamber between a sample source and the chamber, a collection point and the chamber, or between both sample source and collection point. A manifold is not required for all embodiments of the invention.

In the process of filling the chamber with sample the fluid may splash and penetrate into the air of the chamber. Such splashing may cause hydrodynamic stress to the cells or result in foaming or the generation of air bubbles in the cells suspension. It is generally accepted that both hydrodynamic stress and foaming or air bubbles are best avoided when handling living cells. Liquid splashing and hydrodynamic stress and air bubble formation may become a problem in cases when elevated throughput of electroporation process is desired. If a user wants to minimize the time it takes to fill and empty the chamber with cell suspension, a flow rate could be chosen that would lead to liquid splashing and its negative consequences, which would be more significant than any advantage gained by a faster filling rate. As shown below, under certain conditions the liquid may squirt into the chamber from an inlet port and penetrate into other compartments of the system where its presence is not wanted. One way to avoid this problem can be accomplished in a straightforward way by drawing on the well developed art of hydrodynamics or by constructing a test chamber whereby flow of input cell suspension can be observed, such as by making the surface of the chamber from a transparent material. With such a test chamber splashing or generating air bubbles or foam could be observed and flows that result in splashing or air bubble or foaming could be avoided.

In one treatment of the potential splashing problem, a small volume (a separate drop) of liquid that is leaving an opening of a round pipe placed in the upright position is considered. While in the pipe, the liquid is propelled by the pressure difference across the ends of the pipe being developed by a pump or some other means. When out of the pipe, the liquid continues to move in the direction of flow by inertia. If the flow is directed upward and it is assumed that no forces act on a free drop, the inventors can estimate how far it will travel in the air, using the conservation of energy principle, which states that the sum of kinetic and potential energies of the drop will remain constant (Equation 1):

Equation 1:

$$\frac{mV(t)^2}{2} + mgh(t) = const$$

where m is the mass of the drop,

V(t) is its velocity, g is the acceleration due to gravity and h(t) is the elevation of the drop above the pipe opening.

Since substantially all of the mechanical energy associated with the drop in the moment when it leaves the pipe is the kinetic energy, the constant is equal to $\frac{1}{2} mV_0^2$, where $V_0$ is the average linear velocity of fluid flow, which is equal to the ratio of volumetric flow rate to the channel cross-section. When the drop reaches its highest point, its velocity becomes zero, and its elevation can be found from the relationship (Equation 2). These forces may be taken into account and the design of the system can be optimized by altering the dimensions of the fluid paths, the geometry of the electroporation chamber, and the pressures used to regulate the flow of fluid within the system.

Equation 2:
$$mgh_{max} = \frac{mV_0^2}{2}, \text{ or } h_{max} = \frac{V_0^2}{2g}$$

For instance, let the cell suspension be pumped through a ⅛ inch internal diameter (ID) pipe at 5 mL/s. Its average linear velocity will be then ~63 cm/s, and according to the principles of laminar flow, the maximal linear velocity in the center of the pipe will be twice the average one, giving the value for $V_0$ of 126 cm/s. With the value of g being 980 cm/s² one gets $h_{max}$=8 cm. This distance is comparable with the characteristic dimension of the processing chamber, therefore splashing may be possible at the indicated conditions.

Solutions to a potential splashing problem include, but is not limited to the following example. A two-fold increase in the flow rate will result in a four-fold increase of $h_{max}$: the jet height in the example above will be >30 cm at 10 mL/s flow rate, meaning that the cell suspension will be definitely brought into the chamber through a jet and not by a gentle flow. On the other hand, a two-fold increase in the tubing cross-section will result in a four-fold decrease of the jet height, so given the required flow rate one should choose the diameters of supply tubing and inlet ports as large as reasonable in order to minimize the splashing and disturbance of cells in suspension. Given this theoretical treatment of the problem, more empirical solutions may be identified by various combination of flow rates, port dimensions, fluid paths and the like.

Figure 2:
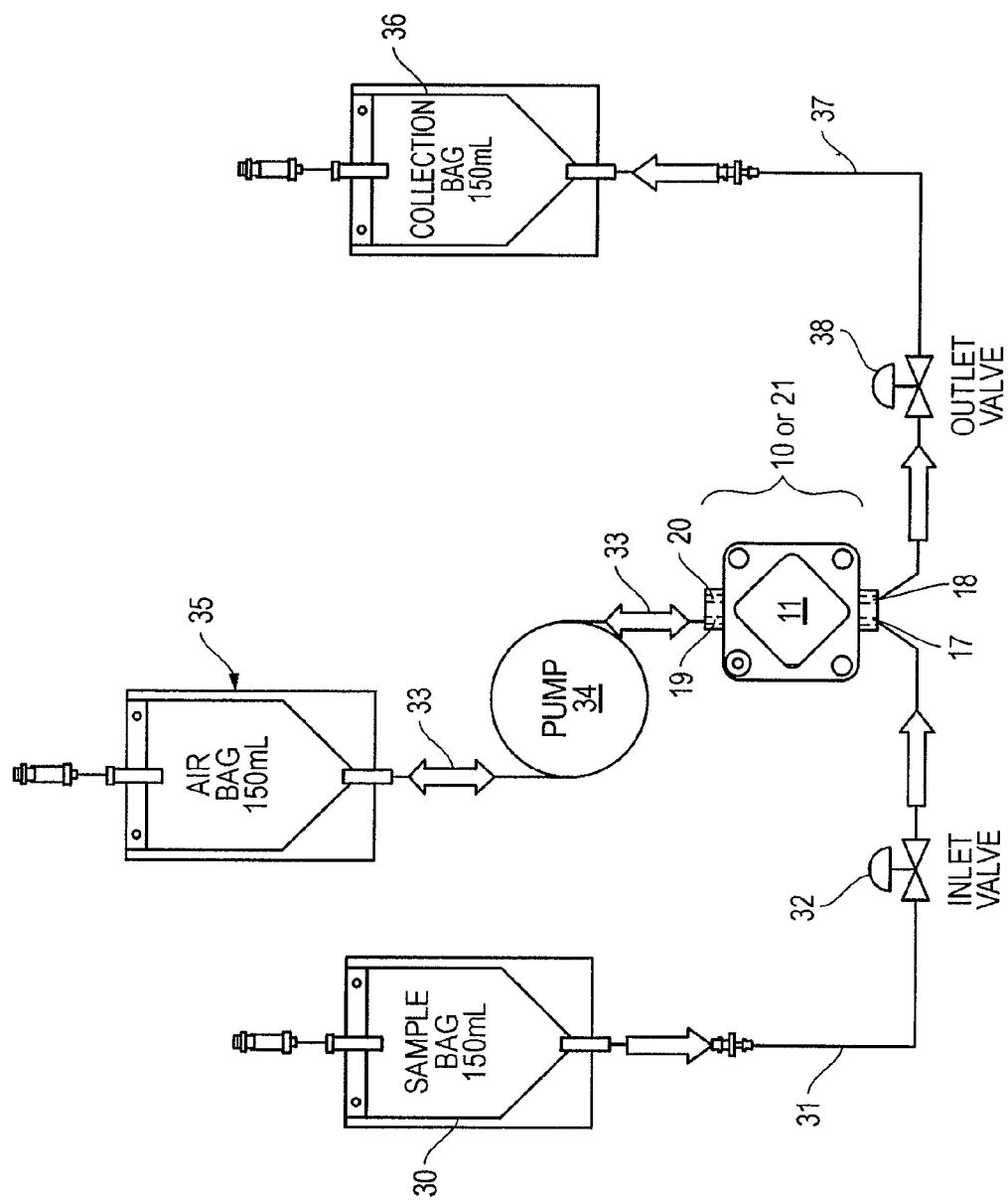
FIG. 2 is a is a schematic of a first exemplary configuration for an electroporation process.

Methods of the invention may be carried out using a variety of device configurations. In a first example, a device configuration may include an electroporation chamber of FIG. 5 or FIG. 8 or modification thereof. With reference to FIG. 2, a sample source 30 is in fluid communication with the chamber 11 by a first fluid path 31, which is coupled to the chamber through chamber port 17. Flow from the sample source 30 to the chamber 11 is regulated, as is exemplified by a valve 32. The chamber 11 is coupled to the processed sample depot 36 by a second fluid path 37 through a second port 18. Flow within fluid path 37 can be regulated by a second valve 38. A non-sample fluid or gas source 35 is in fluid communication with the chamber 11 by a third fluid path 33. Fluid path 33 provides fluid communication between the non-sample gas or fluid depot 35 and the chamber 11. The third fluid path 33 includes a pump 34 or other means of motive force for moving fluids within the fluid paths operatively coupled thereto. The third fluid path 33 is coupled to the chamber 11 by a third port 19.

An exemplary initial configuration of the system diagramed in FIG. 2 may be that the chamber 11 contains a non-sample fluid or gas and the sample source 30 includes a solution of target cells, target substance(s), reagents or various combinations thereof. With valve 32 open and valve 38 closed, the pump 34 can evacuate the non-sample fluid or gas from the chamber 11. Alternatively, the sample may be pumped into the chamber displacing or compressing the non-sample fluid or gas. As the non-sample gas leaves the chamber 11, or is compressed in the chamber, the sample from the sample source 30 flows into the chamber 11. Once the chamber 11 is sufficiently filled with the sample, an electric pulse is sent through the chamber by the use of electrodes. Once exposed to the electric current the sample is considered a processed sample. With valve 32 closed and valve 38 open, the non-sample fluid or gas is pumped or caused to move into the chamber 11. The non-sample fluid or gas may be actively pumped into the chamber or drawn into the chamber by the evacuation of the processed sample. The processed sample flows through fluid path 37 to the depot or collection point exemplified by a collection bag 36. This process may be cycled through a number of times, with or without modification of the electric pulse characteristics, until all or part of the starting sample volume has been processed.

Figure 3:
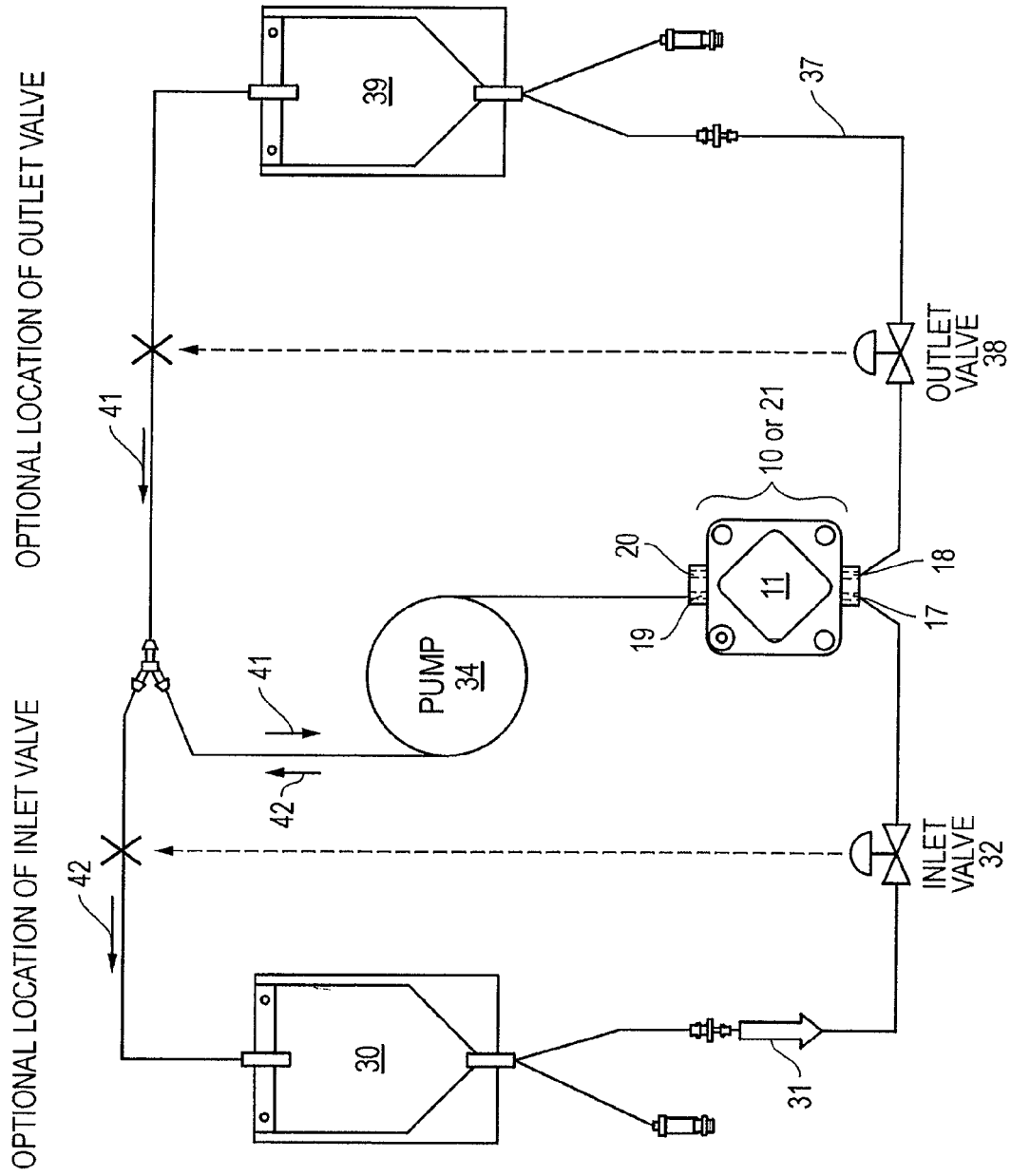
FIG. 3 is a is a schematic of a second exemplary configuration for an electroporation process.

In reference to FIG. 3, a further embodiment of the invention may include a sample source 30 in fluid communication with a chamber 11 by the fluid path 31, which is coupled to the chamber 11 through chamber port 17. Flow from the sample source 30 to the chamber 11 is regulated, as is exemplified by valve 32. A non-sample fluid or gas source is combined with a processed sample depot or collection point to form a non-sample fluid or gas/processed sample depot 39. The chamber 11 is coupled to the non-sample fluid or gas/processed sample depot 39 by a second fluid path 37 through a second port 18. A second valve 38 can regulate flow within fluid path 37. The non-sample fluid or gas/processed sample depot 39 is in fluid communication with the chamber 11 by a third fluid path 41. Fluid path 41 is bifurcated between the non-sample fluid or gas/processed sample depot 39 and the pump 34 forming a fourth fluid path 42. The third fluid path 41 is operatively coupled to a pump 34 or other means of moving fluids within the fluid paths. The third fluid path 41 is coupled to the chamber 11 by the third port 19.

An exemplary initial configuration of the system diagramed in FIG. 3 may be that the chamber 11 and non-sample fluid or gas/processed sample depot 39 contain a non-sample fluid or gas and the sample source 30 contains a solution of target cells, reagents, target substance(s) or various combinations thereof. With valve 32 open and valve 38 closed, the pump 34 moves the non-sample fluid or gas from the chamber 11 through fluid path 42 and into the sample source 30. As the non-sample gas leaves the chamber 11 the sample from the sample, source 30 flows into the chamber 11. Once the chamber is sufficiently filled with the sample, an electric pulse is sent through the chamber by the use of electrodes. Once exposed to the electric current the sample is considered a processed sample. With valve 32 closed and valve 38 open, the non-sample fluid or gas is pumped into the chamber 11 from non-sample fluid or gas/processed sample depot 39 through fluid path 41. The processed sample flows through fluid path 37 to the non-sample fluid or gas/processed sample depot 39. This process may be cycled through a number of times until all or part of the starting sample volume has been processed.

Figure 4:
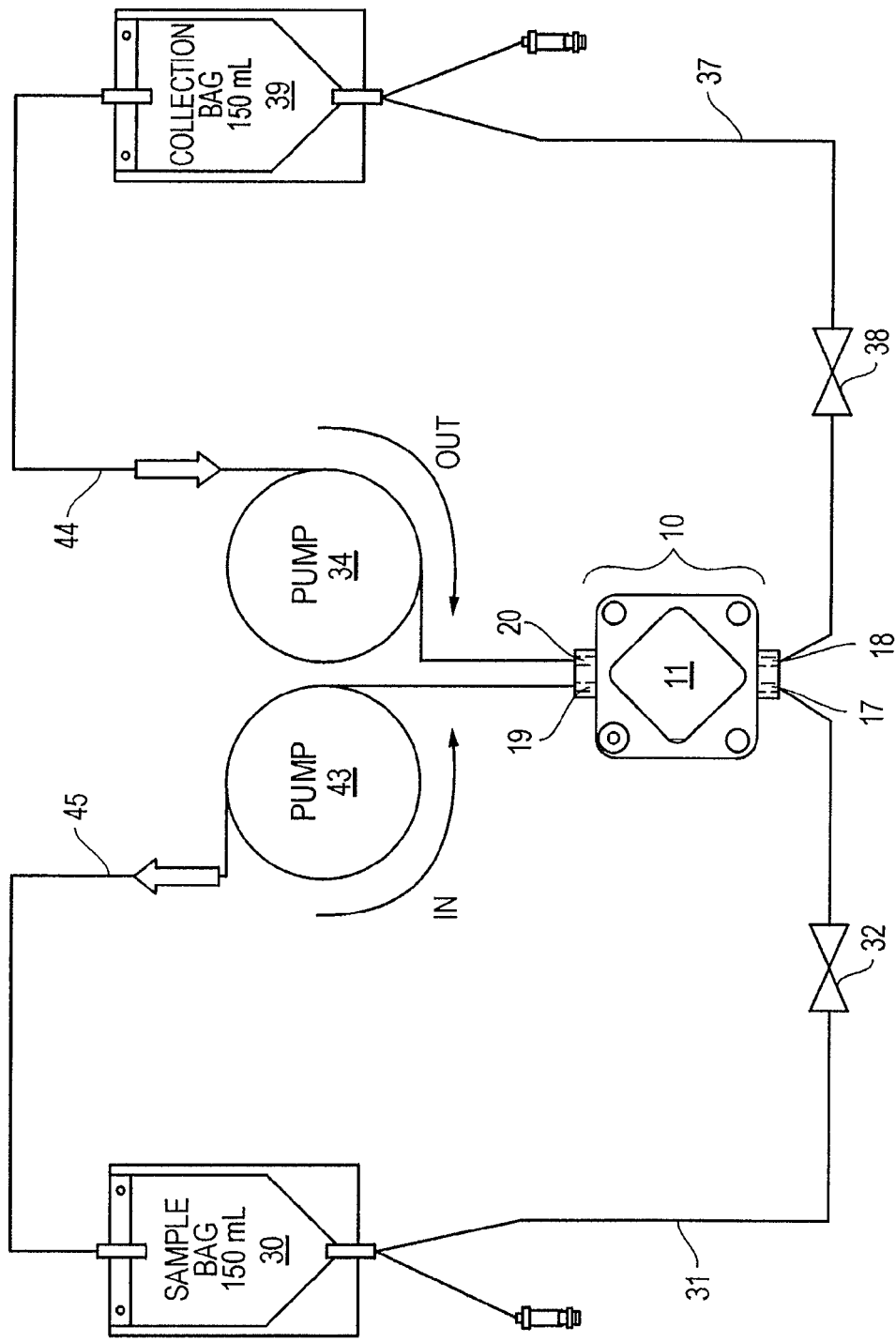
FIG. 4 is a schematic of a third exemplary configuration for an electroporation process.

In still further embodiments, the electroporation chamber 10 may be included in the configuration depicted in FIG. 4. With reference to FIG. 4, a sample source 30 is in fluid communication the chamber 11 by the fluid path 31, which is coupled to the chamber through chamber port 17. Flow from the sample source 30 to the chamber 11 may be regulated by valve 32, valve 32 is optional, or pump 43. The chamber 11 is coupled to the non-sample fluid or gas/processed sample depot 39 by a second fluid path 37 through a second port 18. Flow within fluid path 37 may be regulated by a second valve 38 (optional), or by first pump 34. A non-sample fluid or gas source is combined with a processed sample depot or collection point to form a non-sample fluid or gas/processed sample depot 39. The non-sample fluid or gas/processed sample depot 39 is in fluid communication with the chamber 11 by a third fluid path 44. The third fluid path 44 is operatively coupled to a first pump 34 or other means of moving fluids within the fluid paths. The third fluid path 44 is coupled to the chamber 11 by a fourth port 20. Chamber 11 is coupled to the sample source 30 through port 19 and a fourth fluid path 45. A second pump 43 is operatively coupled to the fourth fluid path 45.

An exemplary initial configuration of the system diagramed in FIG. 4 may be that the chamber 11 and non-sample fluid or gas/processed sample depot 39 contain a non-sample fluid or gas and the sample source 30 contains a solution of target cells, reagents, target substance or various combinations thereof. With valve 32 open and valve 38 closed, or a first pump 34 inhibiting flow in the second 37 and third 44 fluid paths, a second pump 43 may move the non-sample fluid or gas from the chamber 11 through fluid path 45 and into the sample source 30. As the non-sample gas leaves the chamber 11 the sample from the sample, source 30 flows into the chamber 11 through fluid path 31. Once the chamber is filled with the desired volume of sample, an electric pulse is sent through the chamber by the use of electrodes. Once exposed to the electric current the sample is considered a processed sample. With valve 32 closed or second pump 43 inhibiting flow in the first 31 and fourth 45 fluid paths and valve 38 open, the non-sample fluid of gas is pumped by the first pump 34 into the chamber 11 from non-sample fluid or gas/processed sample depot 39 through fluid path 44. The processed sample flows through fluid path 37 to the non-sample fluid or gas/processed sample depot 39. This process may be cycled through a number of times until all or part of the starting sample volume has been processed.

II. Description of Flow Electroporation Device

An electroporation chamber assembly may be used to selectively fractionate biological units, such as cells, that are introduced from an exterior source into an electroporation chamber assembly. The biological units may then be subjected to electroporation in the presence of a biological or chemical substance, causing the substance to enter transiently opened pores in the membranes of the biological units. Once electroporated, the biological units are removed from the electroporation chamber to permit further handling of the electroporated cells and to allow for the electroporation of a new fraction, portion or unit volume of cell suspension. A detailed description of the structure and construction of the electroporation chamber according to exemplary embodiments of the present invention is provided below.

Certain embodiments of the invention include an electroporation chamber for electrical treatment of suspensions of particles, especially living cells, comprising an electroporation chamber having one or more inlet flow ports, one or more outlet flow ports. The electroporation chamber is comprised of two or more walls, with the chamber further being configured to receive and transiently contain a sample, e.g., cells in suspension, or a non-sample fluid or gas from one or more inlet flow ports. The chamber also includes paired electrodes disposed in relation to the chamber such that each electrode forms at least one wall of the chamber. Each electrode is in electrical communication with a source of electrical energy, whereby suspensions of cells flowing through the chamber may be subjected to an electrical field formed between the electrodes.

An exemplary electroporation chamber of the invention is shown in FIG. 5. With reference to FIG. 5, the electroporation chamber 10 includes a chamber 11. The walls 12 define the chamber and a gasket 13 positioned between the walls 12. The walls 12 may be electrode plates. The gasket 13 is designed to provide a space between the walls 12 to form the chamber 11. The walls 12 and the gasket 13 are held by a fastening means 14, which may have an associated electrode gap spacer 15. The fastening means 14 may include, but is not limited to a bolt, a clip, a pin, a molded material, such a molded plastic, and the like. In the embodiment shown in FIG. 5, the electroporation chamber 10 has four ports: a first port 17, a second port 18, a third port 19, and a fourth port 20, in certain embodiments the fourth port 20 is optional. Each of the ports may be in fluid communication with a sample source, a non-sample fluid or gas, a reagent source, a depot for processed sample or various containers for various solutions and reagents.

Figure 6:
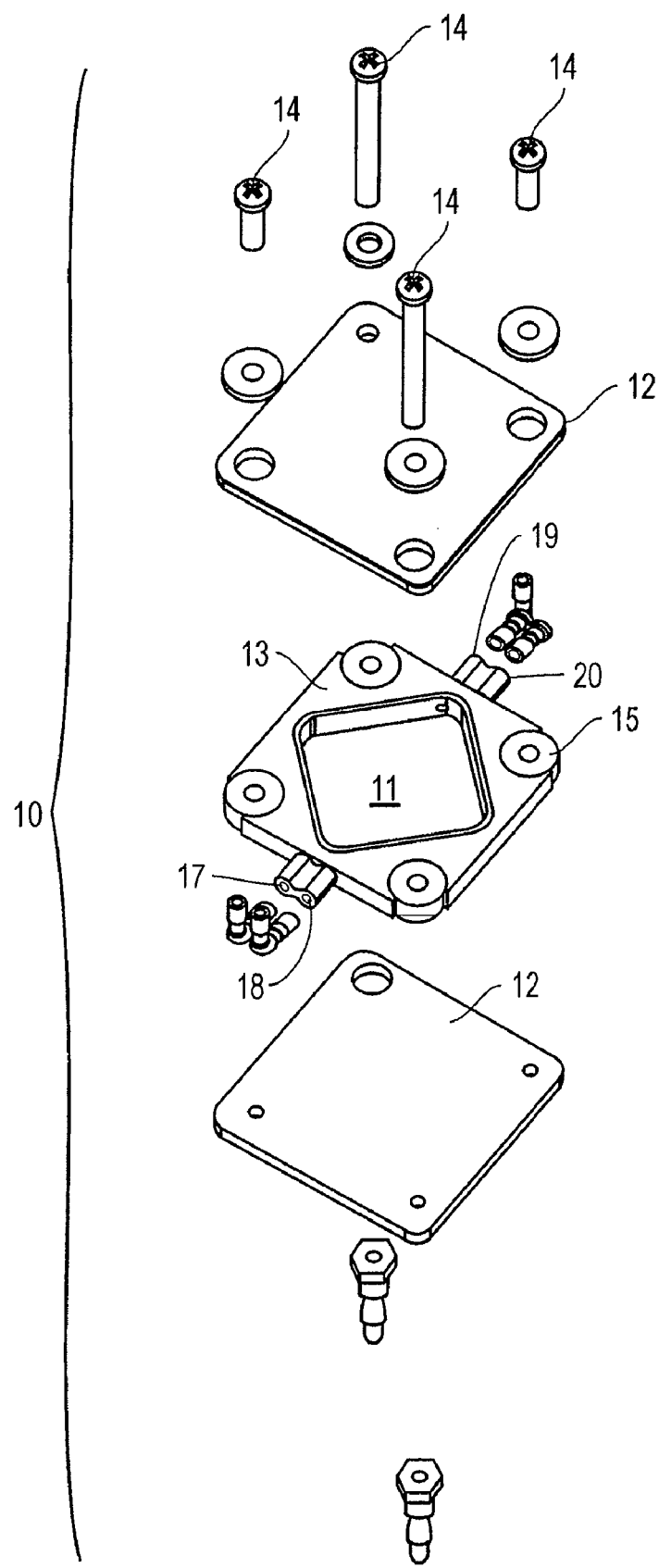
FIG. 6 is an exploded view of one embodiment an electroporation chamber.

An exploded view of electroporation chamber 10 illustrated in FIG. 5 is provided in FIG. 6. With reference to FIG. 6, the electroporation chamber 10 includes a chamber 11. The chamber 11 is defined by the walls/electrode 12 of the chamber and a gasket 13 positioned between the walls. The gasket 13 is designed to provide a space between the walls 12 to form the chamber 11. The walls 12 and the gasket 13 are held by a fastening means 14, which may have an associated spacer 15. The fastening means 14 may include, but is not limited to a bolt, a clip, a pin, a molded material, such a molded plastic, and the like. In the embodiment shown in FIG. 6, the chambers has four ports: a first port 17, a second port 18, a third port 19, and a fourth port 20, in certain embodiments the fourth port 20 is optional. Each of the ports may be in fluid communication with a sample source, a non-sample fluid or gas, a reagent source, a depot for processed sample or various containers.

Figure 7:
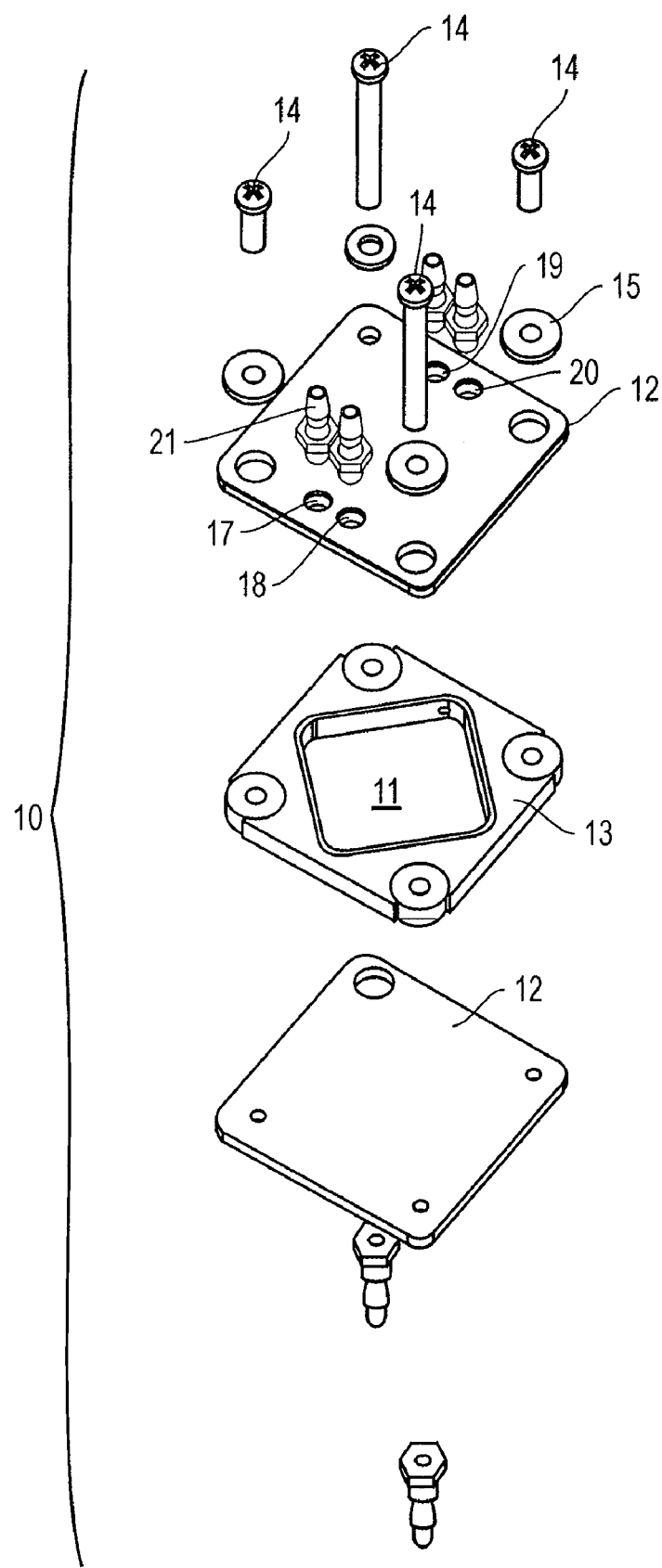
FIG. 7 is an exploded view of an alternative embodiment an electroporation chamber.

An exploded view of alternative embodiment of the electroporation chamber 10 is provided in FIG. 7. With reference to FIG. 7, the electroporation chamber 10 includes a chamber 11. The chamber 11 is defined by the walls/electrode 12 of the chamber and a gasket 13 positioned between the walls. The gasket 13 is designed to provide a space between the walls 12 to form the chamber 11. The walls 12 and the gasket 13 are held by a fastening means 14, which may have an associated spacer 15. The fastening means 14 may include, but is not limited to a bolt, a clip, a pin, a molded material, such a molded plastic, and the like. In the embodiment shown in FIG. 5, the chambers has four ports: a first port 17, a second port 18, a third port 19, and a fourth port 20, in certain embodiments the fourth port 20 is optional. In this embodiment, the plane of the port (17, 18, 19, 20) bore is in the same plane as the plane of the walls 12 of the chamber 11. Each of the ports may be in fluid communication with a sample source, a non-sample fluid or gas, a reagent source, a depot for processed sample or various containers.

Figure 8:
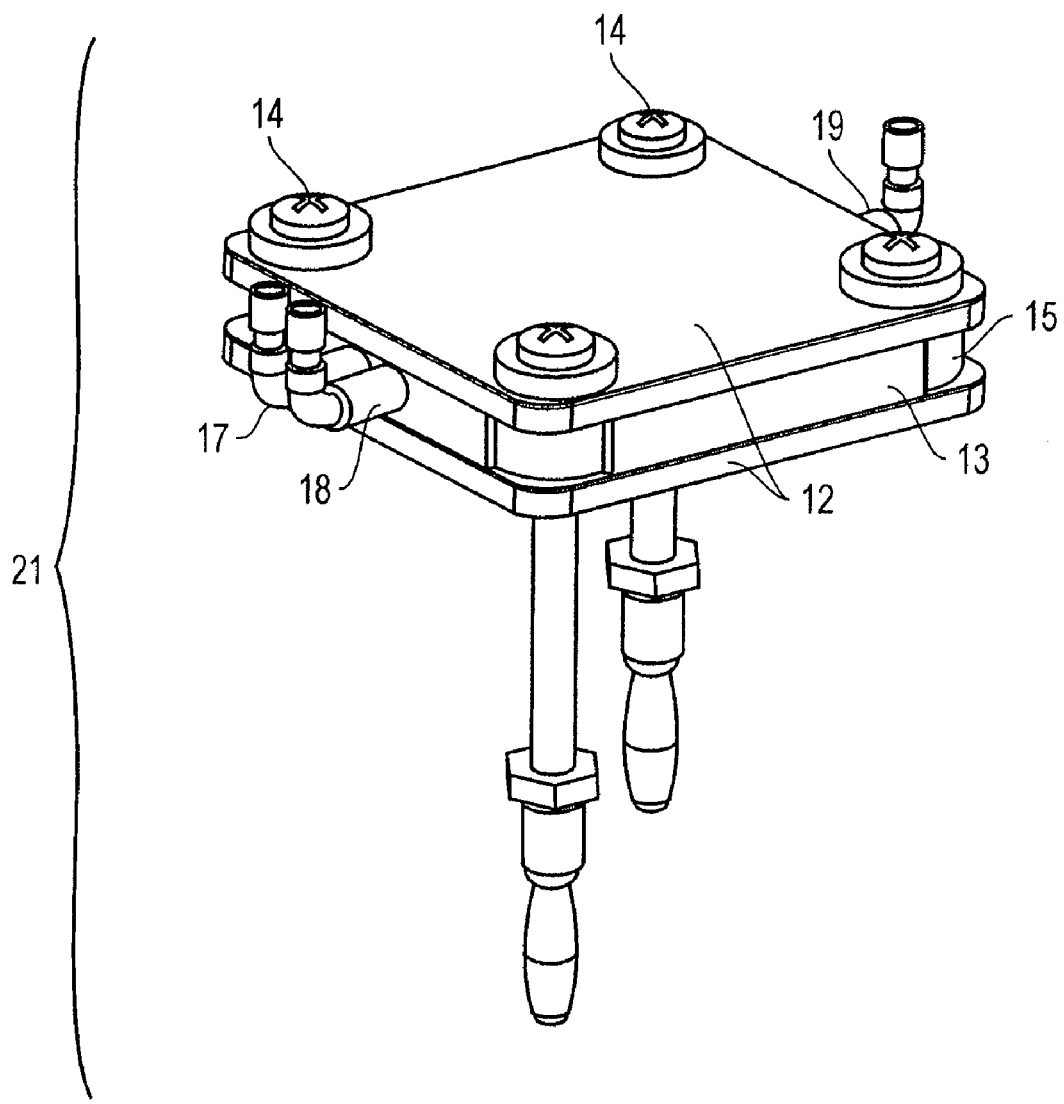
FIG. 8 is a perspective view of another disclosed embodiment of an electroporation chamber of the present invention.

Another embodiment of an electroporation chamber is shown in FIG. 8. With reference to FIG. 8, the electroporation chamber 21 includes three ports (17, 18, and 19). The walls 12 define the chamber and a gasket 13 positioned between the walls 12. The walls 12 may be electrodes or have electrodes incorporated therein. The gasket 13 is designed to provide a space between the walls 12 to form the chamber 11. The walls 12 and the gasket 13 are held by a fastening means 14, which may have an associated spacer 15. The fastening means 14 may include, but is not limited to a bolt, a clip, a pin, a molded material, such a molded plastic, and the like. In the embodiment shown in FIG. 8, the chamber has three ports: a first port 17, a second port 18, and a third port 19. Each of the ports may be in fluid communication with a sample source, a non-sample fluid or gas, a reagent source, a depot for processed sample or various containers as described below.

Figure 9:
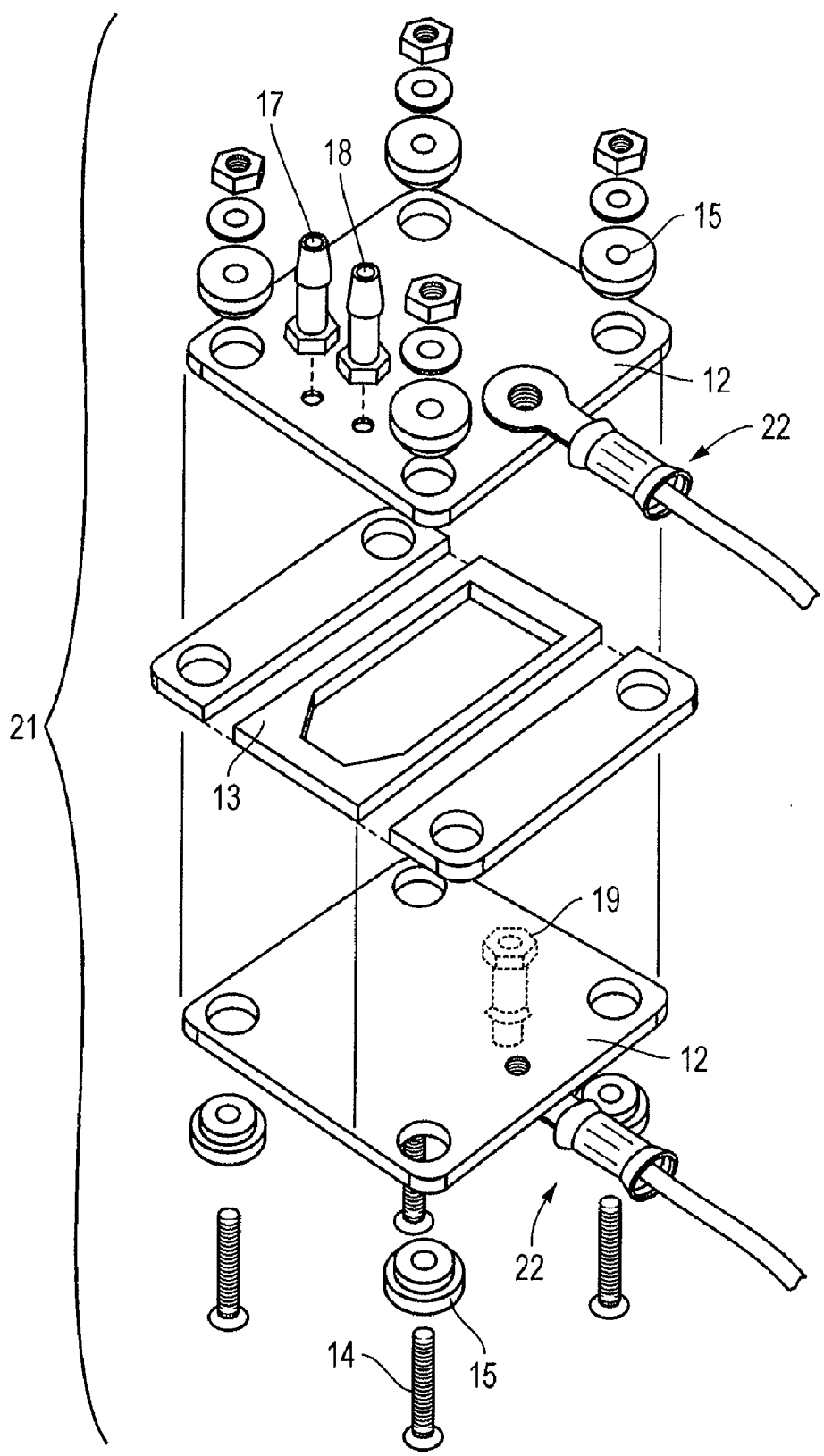
FIG. 9 is an exploded perspective view of another disclosed embodiment of an electroporation chamber of the present invention.

With reference to FIG. 9, an exploded view of FIG. 8, the electroporation chamber 21 includes a chamber 11 and three ports (17, 18, and 19). The chamber is defined by the walls 12 and a gasket 13 positioned between the walls 12. The walls 12 may be electrodes or have electrodes incorporated therein. The gasket 13 is designed to provide a space between the walls 12 to form the chamber 11. The walls 12 and the gasket 13 are held by a fastening means 14, which may have an associated spacer 15. The fastening means 14 may include, but is not limited to a bolt, a clip, a pin, a molded material, such a molded plastic, and the like. In the embodiment shown in FIG. 5, the chamber has three ports: a first port 17, a second port 18, and a third port 19. Each of the ports may be in fluid communication with a sample source, a non-sample fluid or gas, a reagent source, a depot for processed sample or various containers.

In embodiments of the present invention as shown in FIG. 5-9, a gasket 13 containing a chamber 11 may be positioned between the electrode plates 12, with the thickness of the gasket 13 equal to the thickness of the electrode gap spacers 15. The gasket 13 typically forms a seal with the opposing electrode plates 12. The gasket 13 may be constructed of silicone, other synthetic or natural rubbers or other polymers, or other electrically non-conductive materials. Integral within the gasket 13, one or more chambers 11 may be provided. A square, rectangle, channel, or other cutout within the gasket 13 defines the chamber 11. The size and shape of the chamber 11 is proportional to the size and shape of the electrode plates 12.

Also referring to FIG. 5-9, an electroporation chamber 10 or 21 may be constructed of two opposing electrode plates 12. Typically, the electrode plates 12 may be constructed of iron, steel, copper, aluminum, or other electrically conductive metals or metal alloys. The electrode plates 12 may further be coated with gold, platinum, zinc, carbon, or other plating materials to enhance their electrical conductivity. Each electrode plate 12 may be provided with one or more electrical terminals 22 that interface with the power supply circuitry of the overall flow electroporation system.

Figure 14:
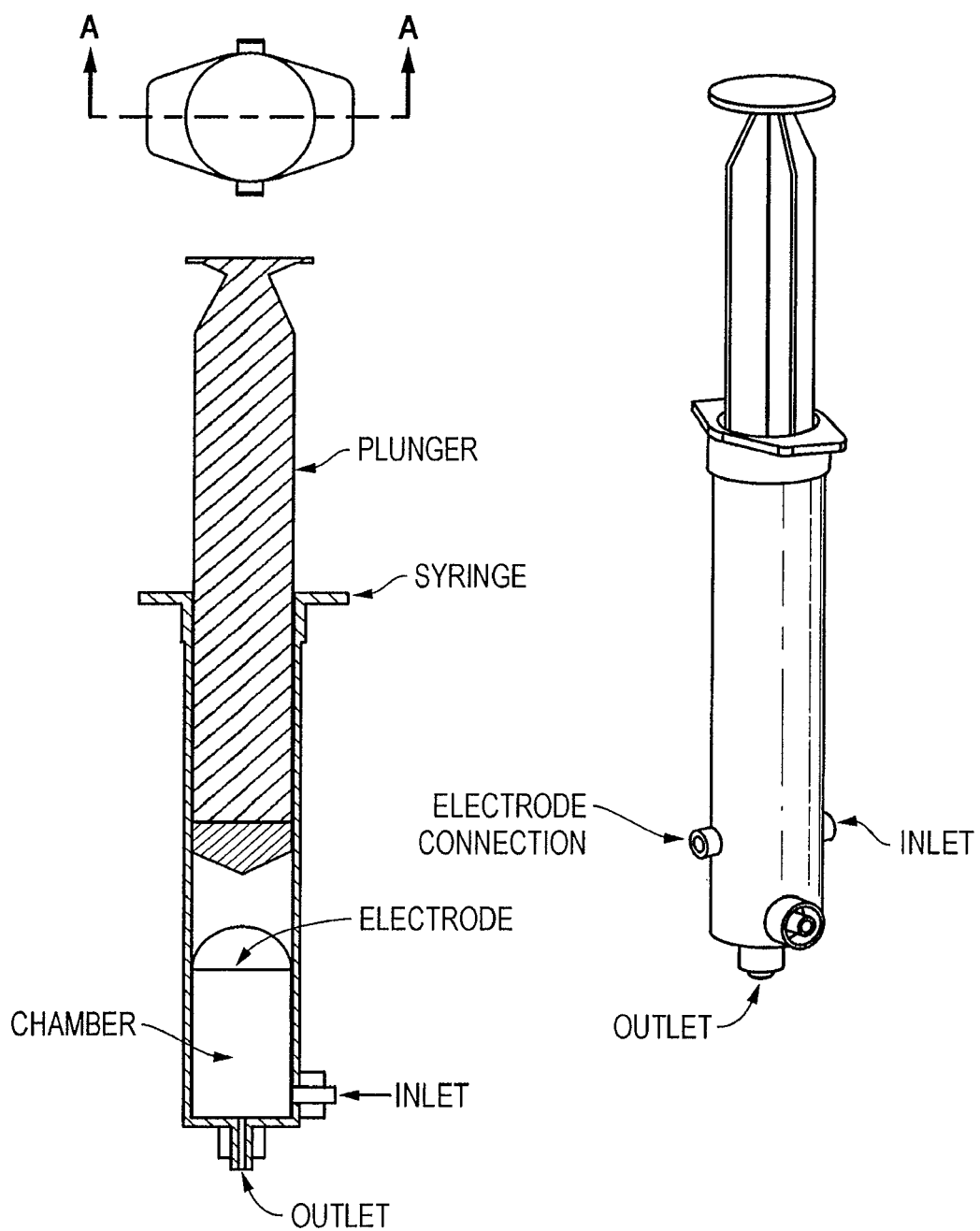
FIG. 14 illustrates an alternative embodiment of the invention that includes a plunger type pumping means.

The electrode plates 12 may typically be separated by one or more electrode gap spacers 15. The thickness of the electrode gap spacers 15 will define and fix a gap between the electrodes 12. The gap between the electrodes 12 can easily be adjusted to any desired measurement simply by changing the gap spacers 15. The thickness of one such gap will vary depending on the flow volume and field strength, but will generally be greater than 3 mm, preferably approximately 0.01 mm to approximately 2 cm, especially preferably approximately 0.1 mm to 1 cm. In other embodiments, the gap may be greater than 3 mm, preferably about 4 mm to about 2 cm, especially about 5 mm to about 1 cm. FIG. 14 illustrates an example of an alternative embodiment of the invention in which a plunger device with at least one port is used as an electroporation chamber as described herein. In this particular type of device, the plunger may be used to displace the sample volume. A non-sample gas or liquid is not required in a device or a method based on the basic principle illustrated.

The electrode gap spacers 15 are typically constructed of an electrically insulating material, and may be fashioned from such materials as plastic, ceramic, rubber, or other non-conductive polymeric materials or other materials.

In one embodiment, the electroporation chamber assembly includes electrode plates 12 that may contain one or more portal bores. Each portal bore may further contain either a flow inlet, a flow outlet, or a non-sample fluid or gas inlet/outlet, which serve to connect to and interface with the respective inflow/outflow fluid pathways of the overall flow electroporation device.

The electroporation chamber may also contain one or more attachment means to allow their secure assembly. In various embodiments of the present invention, the attachment means 14 may include fasteners such as screws, bolts, rivets, rods, or clips which may be employed to secure the desired positions of the electrode plates 12 with the gasket 13 and chamber 11 interposed therewithin. In still other alternate embodiments of the electroporation, chamber 11 according to the present invention, the attachment means 14 may be secured by adhesives, other bonding techniques, or encapsulation.

The attachment means may be an attachment bore, sized and positioned to receive bolts. Such bolts may be directly placed through the attachment bores, or may be received within plate bushings, and the bolts may be secured by nuts that serve to secure the electroporation chamber. In embodiments that employ conductive electrode gap spacers, electrical insulation of the opposing plate electrodes may be achieved by the use of insulating plate bushings.

In further embodiments, one or both of the opposing electrode plates 12 may further be provided with an interface having a cooling element. The cooling element may be a thermoelectric cooling element, or may provide cooling by direct water or other coolant contact, by ventilation through a heat sink, or other cooling means to dissipate heat generated in the electroporation process, which is typically an exothermic process.

Figure 15C:
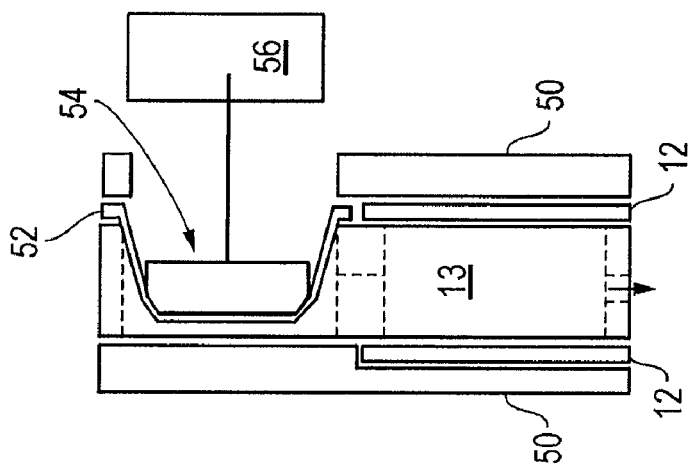
FIG. 15 illustrates a closed, disposable single-stroke pumping system.
Figure 15B:
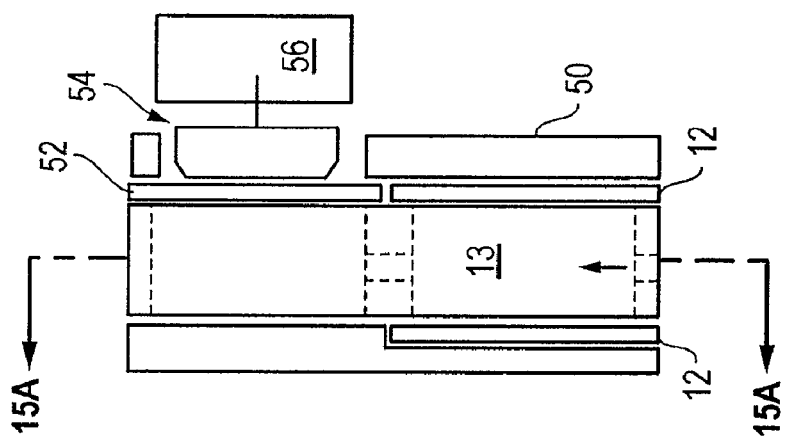
Figure 15A:
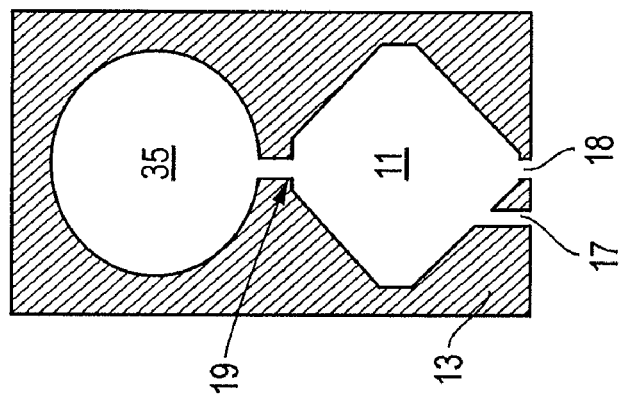

In still a further aspect of the invention, the electroporation chamber may be operably coupled to a closed, disposable single-stroke pumping system that does not require check valves, exemplified in FIG. 15. Many air pumps use a vibrating elastic membrane and require check valves in order to establish a directional air flow. Since various embodiments of the variable flow system have check valves as a part of the system, the process of filling/emptying the electroporation chamber can be accomplished in a single stroke of a piston bending an elastic membrane.

The processing chamber that includes such feature may thus become an inexpensive and fully closed unit that would be capable of a very precise sample movement in a variable flow process. No external pumps will be necessary. In reference to FIG. 15, components of the processing chamber include, but are not limited to a silicone gasket 13, electrodes 12, a plastic body 50; and an elastic membrane 52. The walls of the electroporation chamber 11 and the non-sample fluid or gas container 35 (see FIG. 2) may be formed by the gasket. The gasket 13 may be of a one piece construction. In such embodiments, there is a piston 54; a compact linear actuator 56 controlled by a stepper motor and a computer on the face of the instrument. Embodiments of the invention incorporating such a single stroke piston mechanism may include two pinch valves, as previously described in FIG. 2 (valve 32 and 38). An exemplary positioning of ports 17, 18 and 19, is also shown in FIG. 15.

The specific embodiments illustrated are exemplary of the invention and must not be construed as limiting the invention to the specific examples.

Figure 10:
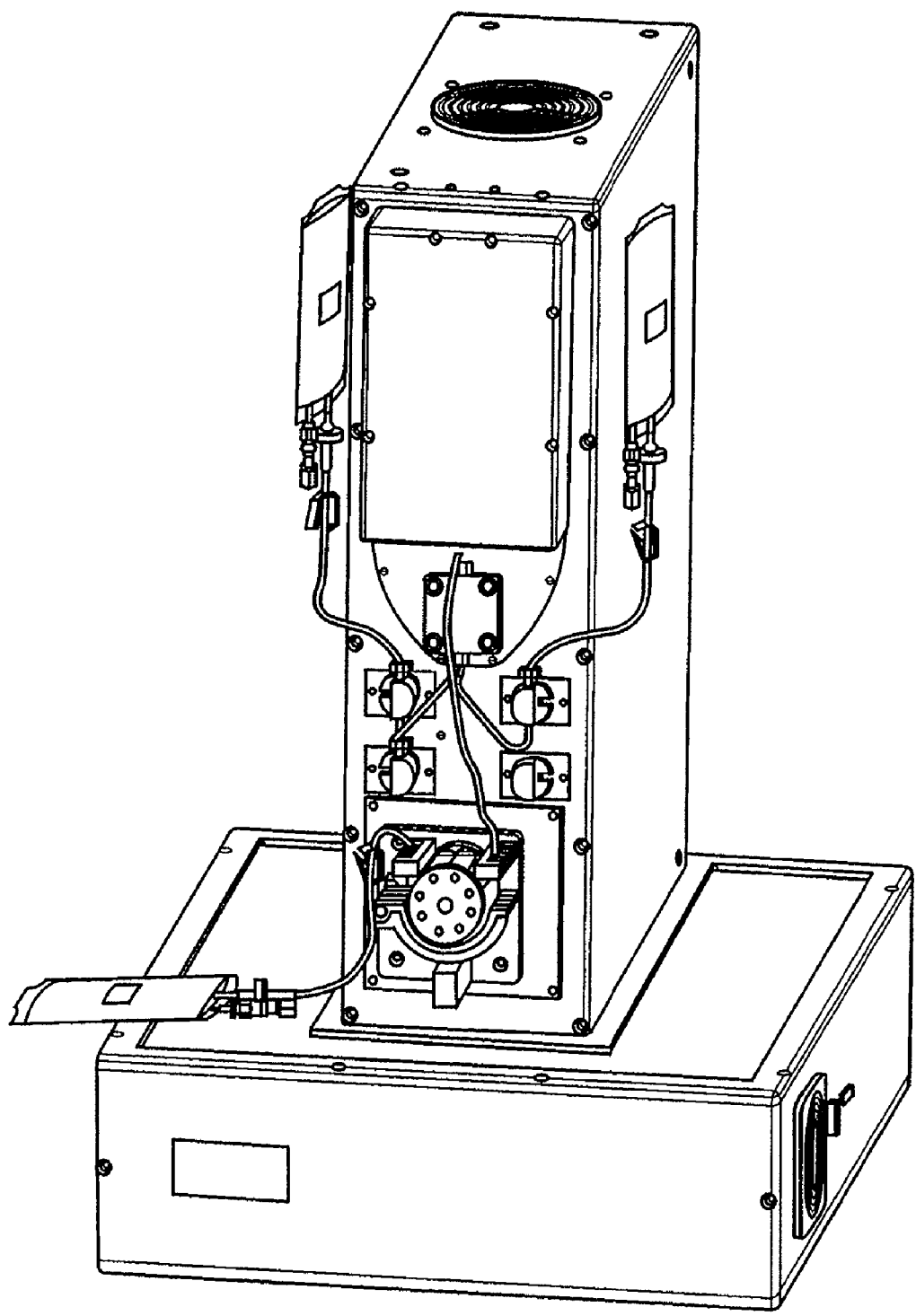
FIG. 10 is a schematic of the electroporation chamber incorporated into an electroporation device.

Certain aspects of the invention include the incorporation of the electroporation chamber of the invention and the various processing configurations into an electroporation device (FIG. 10). In certain embodiments of the invention the flow electroporation device of the present invention may comprise the following: a subassembly that may include an electroporation chamber; the various containers for the sample, processed sample and non-sample fluid or gas, as well as other reagents that may be used in conjunction with the invention; and the tubing that provides for the various fluid paths); electronic components and circuitry to provide high voltage pulses; computer that may control the electronic circuitry and the movement of fluids; and a monitor connected to the computer to enable an operator to assess data and provide inputs or programs to the computer.

The present invention uses regulated flow electroporation to develop new electroporation methods and electroporation devices. The methods exemplified and described herein include the regulated flow and electroporation of a cell suspension. A chamber of the invention may be fabricated so that its cost is sufficiently low that it can be used as a disposable unit. Various different configurations of electroporation chambers can be used in the present invention, examples of, which are described herein. During the time when the cell suspension is present between the electrodes, the cell suspension receives one or more electrical pulses having predetermined electrical parameters including voltage, duration, and temporal spacing (if more than one is used). The optimal electrical parameters will be specific to a particular cell type and possibly the molecule one desires to introduce into the cell by electroporation. Suitable electrical parameters are well known in the art and methods to experimentally determine optimal parameters for new cell types are known. An example of parameters that is suitable for many types of mammalian cells is 1 kV/cm, 1 ms pulse width. A molecule, compound, or composition of interest then diffuses into the cell following concentration and/or electrical gradients. The present invention is optionally capable of subjecting the cells to a range of electric field strengths. Generally speaking, field strengths useful in the present invention are greater than approximately 0.5 kV/cm; preferably, approximately 1 kV/cm to 3.5 kV/cm.

The process is initiated by attaching the electroporation chamber to tubing connected to solutions and cell suspensions in the containers, which may be carried out in an aseptic or sterile environment. The electroporation chamber may snap into a holding site on the apparatus and may be secured by closing a hinged panel. A cell suspension and/or other reagents may be introduced by providing the required commands to one or more pumps, valves, or combinations thereof to cause cell suspension to flow into the electroporation chamber at appropriate time and rates. When a portion of the cell suspension is positioned in the electroporation chamber between electrodes, electric pulses of the chosen voltage, duration, and interval are applied to the electrodes and thereby to the cells in suspension. Following application of the requisite electrical pulses, the commands are provided to one or more pumps, valves or combinations thereof to remove the cell suspension from the electroporation chamber. These commands may also provide for the introduction of a new portion of cell suspension into the electroporation chamber. Cell suspension that has been electroporated is collected separate from cells that have not yet been electroporated. The preceding series of events may conveniently be coordinated temporally by a computer connected operably to the electronic circuitry that provides the electrical pulse and to any pumping means, valves or combinations thereof that effect and control the flow of cell suspension into and out of the electroporation chamber. The electrical pulses applied to the cell suspension and the rate and timing of flow of cell suspension into and out of the electroporation chamber may be provided to the computer by an operator through a graphic used interface on a monitor and a keyboard, both operably connected to the computer. Examples of the flow electroporation system of the present invention are now described in detail.

A. Disposable Electroporation Chamber and Associated Components (Disposable Set)

The disposable set may include various containers (e.g., PVC bags), PVC tubing, connectors, silicone pump tubing, and an electroporation chamber as described herein. All plastic components contacting blood or other cell materials may be Medical Grade Class VI materials.

The electroporation chamber (see FIG. 5) may comprise two low carbon steel (99+% Iron) electrodes electroplated with approximately 100 inches of Pure Gold (99.9%). The electrodes are typically 20 mm straight to within 77 μm over their entire length. When the electrodes are placed in parallel, there is a maximum deviation in distance between bar electrodes of 154 μm. During the assembly process, the electrodes are typically inserted into the electrode gasket, which is then sandwiched between the retainer and plate. The nominal gap between the parallel bar electrodes is 3 mm. The electroporation chamber may have an internal volume of approximately 1.6 mL.

The electrodes can be made of any non-conductive material coated with a layer of metal or other electrically conductive compound.

In certain embodiments, there may be 1, 2, 3, 4, 5, 6, or more containers or sources attached to the disposable set. A container includes, but is not limited to a collapsible, expandable or fixed volume container. A first container, referred to herein as the sample source or sample container, contains the cell suspension and may or may not include the substance that will be inserted into the cell via the electroporation process. If the substance to inserted in not included there will be a second container containing this substance, which will be mixed inline before entry into the electroporation chamber or in the electroporation chamber. The first (optionally the second container) is connected to PVC or other suitable tubing lines that pass through any designated pinch valves, if valves are included in the configuration, and flow into a first port (an inlet port) of the electroporation chamber. In certain embodiments, it is contemplated that a single port electroporation chamber may be used in the practice of the invention. Further aspects of the invention may include other containers that connect to the tubing from the sample container and may supply reagents or other samples to the chamber. The converging solutions may be mixed prior, during or after reaching the electroporation chamber.

In still further embodiments, a second port (an outlet port) of the electroporation chamber has at least 1, 2, 3, 4 or more containers attached and may have one or more intervening device to direct flow from the electroporation chamber to an appropriate container. In an additional configuration, a waste container may be attached, which will hold any fluid that the user may wish to discard. A second or third container or bag is referred to as the processed sample or product container. The processed sample or product container will hold cells or other products of the electroporation process.

A third or fourth container may hold various non-sample fluids or gases that are utilized to separate the sample into discrete volumes or unit volumes. The non-sample fluid or gas container is typically connected to the electroporation chamber by a third and/or fourth port. The non-sample fluid or gas container may be incorporated into the processed sample container or the sample container and thus the non-sample fluid or gas is transferred from the processed sample container to another container, which may include the sample source container during the processing of the sample. In certain aspects, the reservoir for containing a non-sample fluid or gas may be incorporated into the chamber, as long as the compression of the non-sample fluid or gas allows the electrode to be positioned appropriately to effect electroporation.

As mentioned earlier, various other containers may be incorporated into the configurations exemplified herein. These additional containers may supply additional reagents, cells, and the like. Additional containers may also provide for a waste container or for containers to segregate processed samples. In various embodiments, an electroporation chamber according to the present invention may contain 1, 2, 3, or more pair of electrodes. In the case where a chamber has more than one pair of electrodes only cell suspension that is substantially between a pair of electrodes when pulses are applied will be efficiently electroporated or electroporated at all. When desirable, multiple electroporation chambers may be provided to achieve more rapid, higher volume electroporation. The term electroporation region as used herein means that portion of the chamber in which material flowing there through is exposed to an electric field of sufficient strength to effect electroporation. In accordance with the present invention, it is desirable that two paired electrodes that define at least a portion of the opposed walls of the electroporation region of the electroporation chamber form a substantial portion of those opposed walls in the electroporation region. As used herein electrodes are said to be a pair if they are positioned so that a substantially uniform electric field exists between them when a voltage differential is applied to the pair. As used herein the term substantial portion shall mean greater than approximately 50%; preferably greater than approximately 60%, more preferably greater than approximately 70%, more preferably greater than approximately 80%, more preferably greater than approximately 90%, most preferably approximately 100%.

Preferably, the electroporation chamber may be provided as a sterile unit for disposable, single-use applications. The components of the electroporation chamber may thus preferably be constructed of materials capable of withstanding sterilization procedures, such as autoclaving, irradiation, or chemical sterilization.

Suitable materials for use in any of the apparatus components as described herein include materials that are biocompatible, approved for medical applications that involve contact with internal body fluids, and should meet US PV1 or ISO 10993 standards. Further, the materials will not substantially degrade, from for instance, exposure to the solvents used in the present invention, during at least a single use. The materials are typically sterilizable either by radiation or ethylene oxide (EtO) sterilization. Such suitable materials include materials that are extrudable if, for instance, used for tubing, and/or injection moldable if, for instance, used for hard containers. Materials useful to form the various components of the apparatus according to the present invention include, but are not limited to, nylon, polypropylene, polycarbonate, acrylic, polysulphone, polyvinylidene fluoride (PVDF), fluoroelastomers such as VITON, available from DuPont Dow Elastomers L.L.C., thermoplastic elastomers such as SANTOPRENE, available from Monsanto, polyurethane, polyvinyl chloride (PVC), polytetrafluoroethylene (PTFE), polyphenylene ether (PFE), perfluoroalkoxy copolymer (PFA) available as TEFLON PFA from E. I. du Pont de Nemours and Company, and combinations thereof.

In many cases, it is important to refer to the throughput of electroporation process, or the amount of cell suspension processed in a certain amount of time. Since it takes a certain amount of energy to electroporate a unit of volume of cell suspension, the more volume of cell suspension electroporated in a given time, the more energy in the same time is consumed. The application of voltage to the cell suspension results in a flow of current through the suspension, which has an electrical resistance. This current flow generates heat according to Joule's Law. As most of the electrical energy provided to the chamber and its contents is converted to heat the relationship of electrical power (P) provided to the chamber and its contents as a function of time and the heat produced in the chamber is $P=Q/t$, where $Q$=heat and $t$=time.

Heat produced by electroporation will raise the temperature of the cell suspension, at least transiently. Since it is not desirable to have the cells reach a temperature in excess of 45° C., it may be advantageous to provide means to cool the cells suspension and the electroporation chamber to avoid having the cells reach an unacceptable temperature. The damaging effects of exposure to such high temperatures are a function of the duration of exposure so cooling that is provided as soon as possible following electroporation is desired. Since in a flow electroporation process in which the electroporation chamber repeatedly receives high voltage pulses, and thereby electrical heating, means to cool the electroporation chamber and electroporated cells is especially important. However, while the cooling is usually provided by bringing cell suspension in immediate contact with metal parts which are in their turn being cooled by Peltier elements or by flow of air or fluid, some principal limitations to the cooling process exist. In many cases the designers of electroporation processes either neglect or overlook the fact that thermal conductivity of metal is much higher that of water (or biological buffer), what means that transfer of heat from the flow channel to the cooling unit is always limited by the heat conductivity of water or, equivalently, the cell suspension itself. In such situation, it is important to choose the proper geometry of the flow channel so that heat transfer is accomplished in the most efficient way.

B. Regulation of Sample Flow

The flow of various fluids and/or gases that may be associated with present invention may be regulated by one or more pumping means, valves, or other means designed to cause, inhibit, or totally block or otherwise regulate flow. This may be accomplished by one or more pumps that pump cell suspension or other fluids into the electroporation chamber, one or more pumps that pump cell suspension or other fluid out of the electroporation chamber, or combinations thereof. Cell suspension may also be caused to flow into an out of the electroporation by pumps or other mechanical devices that change the air pressure or volume inside the electroporation chamber. In certain embodiments, gravity may be used move a unit of sample between a pair of electrodes. Valves that may be used including pinch valves, butterfly valves, and/or ball valves may be used to open and close fluid paths completely or partially. In various embodiments, pumps may be employed to regulate and meter the flow of fluids within a device. The pumping of fluids is common in many devices. Fluids ranging from test samples to various reagents and wash fluids that must be transferred, dispensed or metered, depending on the application. As these devices are designed to use smaller and smaller volumes of fluids, the requirements for very accurate metering pumps become greater.

Fluid transfer is sometimes accomplished using either centrifugal or positive displacement pumps. Centrifugal pumps transfer energy to a fluid via a spinning impeller, converting the impeller energy to fluid pressure, which moves the fluid. These types of pumps are very pressure and fluid dependant and are typically not utilized for metering due to their inability to maintain very accurate flows under changing inlet and discharge conditions. Their advantage lies in providing high flow rates at low pressures.

Positive displacement pumps operate by trapping a fixed volume of fluid and moving this fluid via gears, pistons, diaphragms, vanes, or other devices. These pumps typically operate at lower speeds, are less sensitive to changes in discharge and suction conditions, and allow flow regulation by adjusting speed and displacement. These features have made the positive displacement pump the obvious choice for metering fluids. The metering pump can thus be defined as a positive displacement device designed to provide a very precise and repeatable flow within a specified capacity range. Positive displacement metering pumps are normally classified as rotary or reciprocating. Rotary pumps include gear, lobe, vane, and roller (peristaltic) pumps. Reciprocating pumps include diaphragm, piston, and bellows pumps.

C. Other Components

An electroporation device such as that described herein includes various other components such as one or more electronics module interface, computer, monitor and other electronic circuits and software of which one of skill in the art may readily supply. A general layout of electroporation systems and descriptions of various other components of such systems can be found in Published U.S. Patent Applications Nos. 200400292240, 20030073238, 20030059945, and 20010001064, which are incorporated herein by reference.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Variable Flow Electroporation

Figure 11:
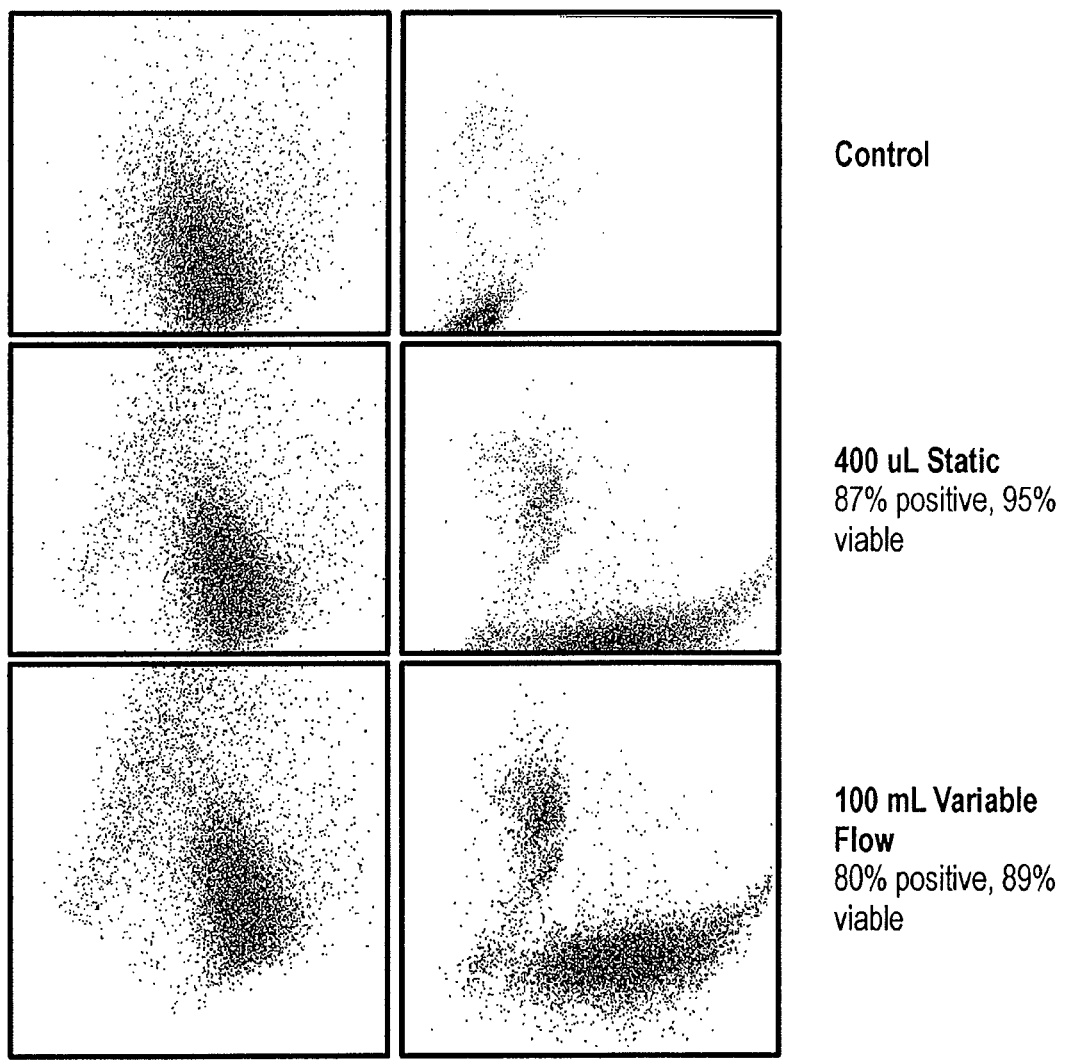
FIG. 11 illustrates a propidium iodide (PI) and GFP fluorescence analysis of Jurkat cells at 24 hours after electroporation.
Figure 12A:
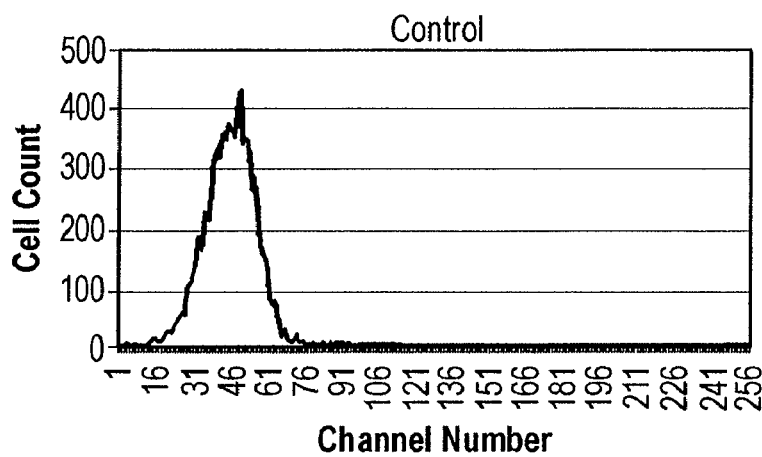
FIGS. 12A-12C illustrates a histogram of fluorescence, as determined by FACS, in Jurkat cells at 24 after electroporation.
Figure 12B:
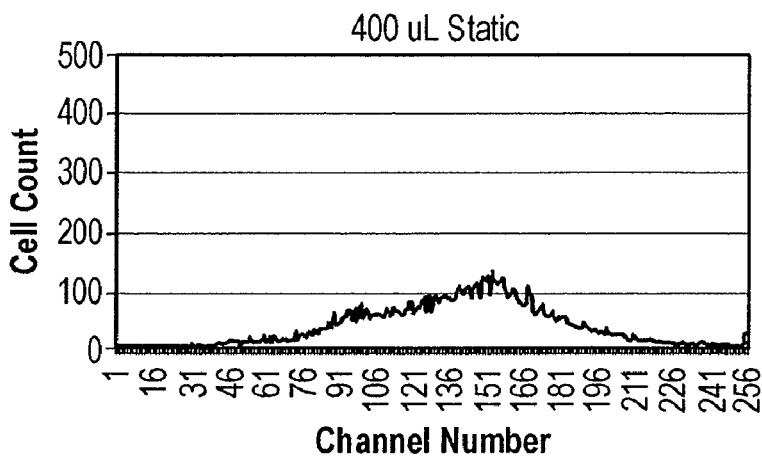
Figure 12C:
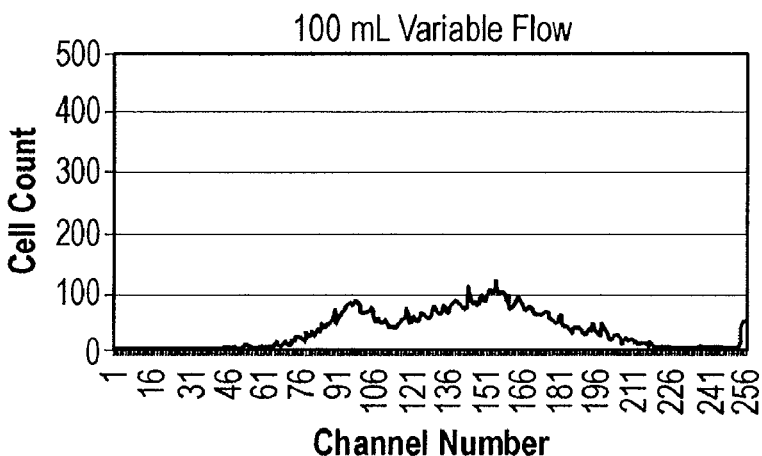
Figure 13:
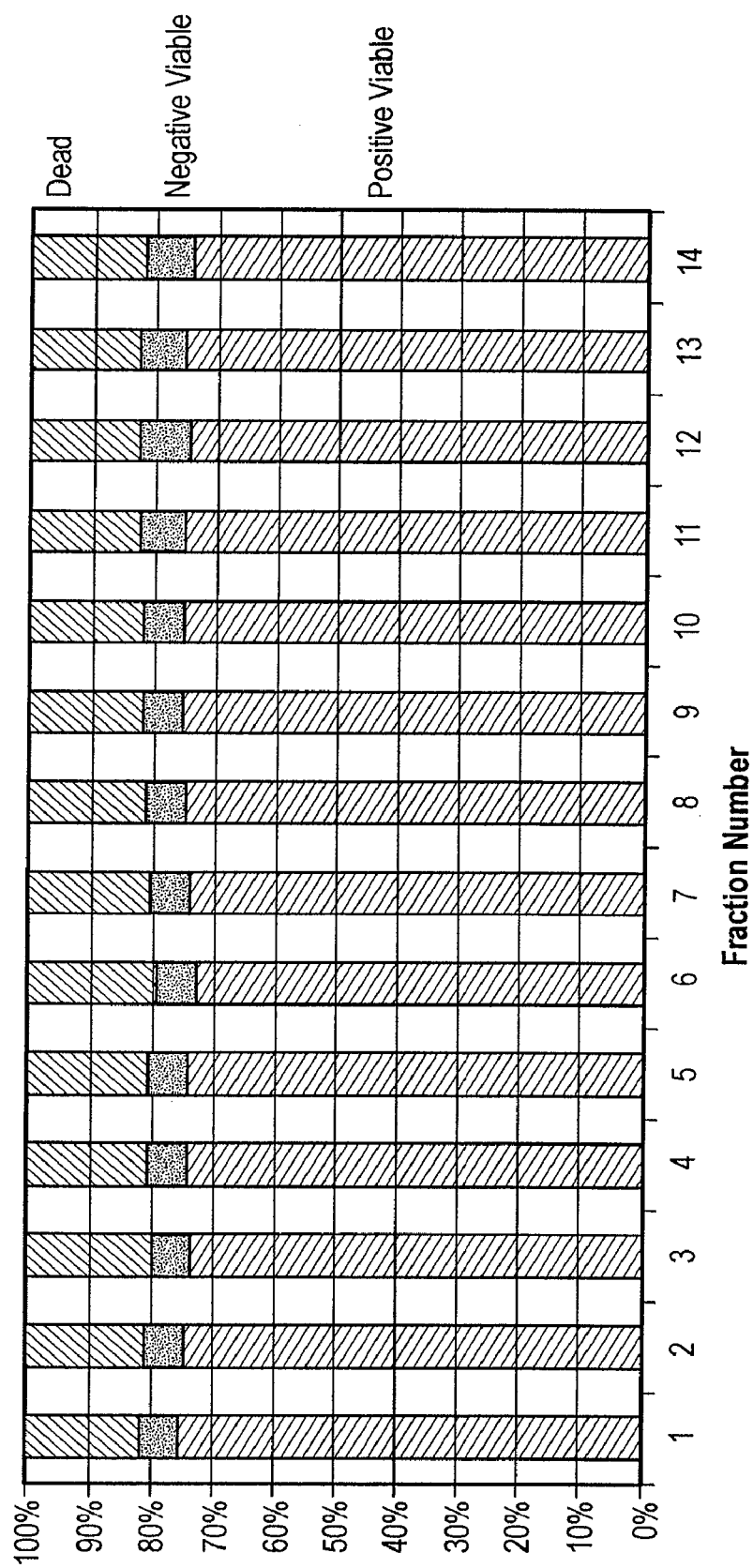
FIG. 13 illustrates an analysis of individual fractions collected at successive cycles of electroporation.

An exemplary electroporation study was conducted using regulated or variable flow electroporation. Jurkat cells were used as a model system and a GFP expressing vector as model compound for transformation. All cell densities were $4 \times 10^7$ Jurkat cells/mL and the plasmid concentration was 100 μg/mL DNA of pTM2 plasmid (~5 Kb) which can express eGFP (green fluorescent protein). The process included removal of a non-sample fluid or gas from a chamber; with the concomitant filling of the chamber with a sample comprising the Jurkat cells and the GFP vector. The unit sample was electroporated during transition from in-flow to out-flow of sample. The processed sample was removed form the chamber with the concomitant in-flow of non-sample fluid or gas. FIG. 11 shows control cells, cells processed using a 400 μL static process, and cells processed using a 100 mL variable flow process assessed for propidium iodide fluorescence or GFP fluorescence. FIG. 12 shows a histogram illustrating the results of FACS analysis for GFP fluorescence in control cells (FIG. 12A), cells processed using a 400 μL static process (FIG. 12B) and cells processed using a 100 mL variable flow process (FIG. 12C). FIG. 13 shows the consistency of results using variable flow electroporation from unit sample to unit sample through 14 consecutive sample fractions. Cells were assessed for GFP transfection and viability, and sorted in to dead cells, viable cells negative for transfection and viable cells positive for transfection.

REFERENCES

The following references, to the extent that they provide exemplary procedural or other details supplementary to those set forth herein, are specifically incorporated herein by reference.

U.S. Pat. No. 4,752,586
U.S. Pat. No. 5,612,207
U.S. Pat. No. 6,074,605
U.S. Pat. No. 6,090,617
U.S. Patent Applications 20010001064
U.S. Patent Applications 20030059945
U.S. Patent Applications 20030073238
U.S. Patent Applications 200400292240

What is claimed is:

1. A flow electroporation device comprising:
   (a) an electroporation chamber having a top and bottom portion containing at least two parallel electrodes, the chamber being formed between the two electrodes and having two chamber ports in the bottom portion of the electroporation chamber and two chamber ports in the top portion of the electroporation chamber;
   (b) at least one sample container that is in fluid communication with the electroporation chamber through a first chamber port in the bottom portion of the chamber and the electroporation chamber is in fluid communication with the sample container through a separate second chamber port in the top portion of the chamber, forming a first fluid path; and
   (c) at least one product container that is in fluid communication with the electroporation chamber through a separate third chamber port in the bottom portion of the chamber and the electroporation chamber is in fluid communication with the product container through a separate fourth chamber port in the top portion of the chamber, forming a second fluid path wherein at least one fluid path is an aseptic fluid path.

2. The device of claim 1, wherein the product container is also used as a non-sample gas reservoir.

3. The device of claim 1, wherein the sample container is also used as a non-sample gas reservoir.

4. The device of claim 1, further comprising at least one pump operatively coupled to at least one fluid path.

5. The device of claim 1, wherein the sample container is collapsible, expandable or fixed volume.

6. The device of claim 1, wherein the product container is collapsible, expandable or fixed volume.

7. The device of claim 1, wherein fluid flow in the device is directed by the opening or closing of one or more fluid paths of the device.

8. The device of claim 1, wherein the first and second fluid path are alternatively open and closed.

9. The device of claim 1, wherein fluid flow is modulated by one or more pumping means.

10. The device of claim 9, wherein the pumping means is a pump.

11. The device of claim 10, wherein the pump is a peristaltic pump.

12. The device of claim 11, wherein the peristaltic pump is a full compression peristaltic pump.

13. The device of claim 1, wherein fluid flow is modulated by valves.

14. The device of claim 13, wherein fluid flow is modulated by a pumping means.

* * * * *